United States Patent
Chennubhotla et al.

(10) Patent No.: US 10,755,138 B2
(45) Date of Patent: Aug. 25, 2020

(54) SYSTEMS AND METHODS FOR FINDING REGIONS OF INTEREST IN HEMATOXYLIN AND EOSIN (H AND E) STAINED TISSUE IMAGES AND QUANTIFYING INTRATUMOR CELLULAR SPATIAL HETEROGENEITY IN MULTIPLEXED/HYPERPLEXED FLUORESCENCE TISSUE IMAGES

(71) Applicant: UNIVERSITY OF PITTSBURGH—OF THE COMMONWEALTH SYSTEM OF HIGHER EDUCATION, Pittsburgh, PA (US)

(72) Inventors: S. Chakra Chennubhotla, Pittsburgh, PA (US); D. Lansing Taylor, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 139 days.

(21) Appl. No.: 15/577,838

(22) PCT Filed: Jun. 10, 2016

(86) PCT No.: PCT/US2016/036825
§ 371 (c)(1),
(2) Date: Nov. 29, 2017

(87) PCT Pub. No.: WO2016/201186
PCT Pub. Date: Dec. 15, 2016

(65) Prior Publication Data
US 2018/0204085 A1    Jul. 19, 2018

Related U.S. Application Data

(60) Provisional application No. 62/174,197, filed on Jun. 11, 2015.

(51) Int. Cl.
*G06K 9/00* (2006.01)
*G06K 9/46* (2006.01)
(Continued)

(52) U.S. Cl.
CPC .......... *G06K 9/469* (2013.01); *G06K 9/0014* (2013.01); *G06K 9/34* (2013.01); *G06K 9/4652* (2013.01);
(Continued)

(58) Field of Classification Search
CPC ........ G06K 9/469; G06K 9/4652; G06K 9/34; G06K 9/0014; G16H 50/20; G16H 30/40;
(Continued)

(56) References Cited

U.S. PATENT DOCUMENTS

| 8,116,551 B2 | 2/2012 | Gallagher et al. |
| 8,559,693 B2* | 10/2013 | MacAulay ............ G06T 7/0012 382/128 |

(Continued)

FOREIGN PATENT DOCUMENTS

| EP | 1662412 A2 | 5/2006 |
| NO | WO 2014/006421 A1 | 1/2014 |

(Continued)

OTHER PUBLICATIONS

P. Isolo et al., Crisp boundary detection using pointwise mutual information. In ECCV 2014, pp. 799-814. Springer, 2104.
(Continued)

*Primary Examiner* — Andrew M Moyer
(74) *Attorney, Agent, or Firm* — Eckert Seamans Cherin & Mellott, LLC; Philip E. Levy

(57) ABSTRACT

Graph-theoretic segmentation methods for segmenting histological structures in H&E stained images of tissues. The method relies on characterizing local spatial statistics in the images. Also, a method for quantifying intratumor spatial
(Continued)

heterogeneity that can work with single biomarker, multiplexed, or hyperplexed immunofluorescence (IF) data. The method is holistic in its approach, using both the expression and spatial information of an entire tumor tissue section and/or spot in a TMA to characterize spatial associations. The method generates a two-dimensional heterogeneity map to explicitly elucidate spatial associations of both major and minor sub-populations.

17 Claims, 14 Drawing Sheets

(51) Int. Cl.
| | | |
|---|---|---|
| G06K 9/34 | (2006.01) | |
| G06T 7/187 | (2017.01) | |
| G06T 7/11 | (2017.01) | |
| G06T 7/162 | (2017.01) | |
| G06T 7/174 | (2017.01) | |
| G16H 30/40 | (2018.01) | |
| G06T 7/00 | (2017.01) | |
| G16H 50/20 | (2018.01) | |

(52) U.S. Cl.
CPC .............. *G06T 7/0012* (2013.01); *G06T 7/11* (2017.01); *G06T 7/162* (2017.01); *G06T 7/174* (2017.01); *G06T 7/187* (2017.01); *G16H 30/40* (2018.01); *G16H 50/20* (2018.01); *G06T 2207/10024* (2013.01); *G06T 2207/10056* (2013.01); *G06T 2207/10064* (2013.01); *G06T 2207/20036* (2013.01); *G06T 2207/30024* (2013.01); *G06T 2207/30096* (2013.01)

(58) Field of Classification Search
CPC ....... G06T 7/0012; G06T 7/174; G06T 7/162; G06T 7/11; G06T 7/187; G06T 2207/30096; G06T 2207/10024; G06T 2207/10056; G06T 2207/30024; G06T 2207/10064; G06T 2207/20036
USPC .................................................. 382/128–134
See application file for complete search history.

(56) References Cited

U.S. PATENT DOCUMENTS

| | | | |
|---|---|---|---|
| 2010/0290692 A1* | 11/2010 | Macaulay | ............. G06T 7/0012 |
| | | | 382/133 |
| 2011/0286654 A1 | 11/2011 | Krishnan | |
| 2014/0003702 A1* | 1/2014 | McCulloch | ........... G06T 7/0012 |
| | | | 382/134 |
| 2015/0154755 A1 | 6/2015 | Wang | |

FOREIGN PATENT DOCUMENTS

| | | | |
|---|---|---|---|
| NO | WO 2015/061631 A1 | 4/2015 | |
| WO | 2013022688 A1 | 2/2013 | |
| WO | 2014055635 A1 | 4/2014 | |

OTHER PUBLICATIONS

European Patent Office, Extended European Search Report for European Application No. 16808345.9, dated Jan. 2, 2019.

Xingyu Li et al., "A Complete Color Normalization Approach to Histopathyology Images Using Color Cues Computed From Saturation-Weighted Statistics", IEEE Transactions on Biomedical Engineering, Feb. 19, 2015, vol. 62, No. 7, pp. 1862-1873.

Allan Hanbury, Circular Statistics Applied to Colour Images, PRIP, TU Wien, Favoritenstraße, 9/1832, A-1040 Vienna, Austria hanbury@prip.tuwien.ac.at; This work was supported by the Austrian Science Foundation (FWF) under grants P14445-MAT and P14662-INF.

* cited by examiner

SYSTEMS AND METHODS FOR FINDING REGIONS OF INTEREST IN HEMATOXYLIN AND EOSIN (H AND E) STAINED TISSUE IMAGES AND QUANTIFYING INTRATUMOR CELLULAR SPATIAL HETEROGENEITY IN MULTIPLEXED/HYPERPLEXED FLUORESCENCE TISSUE IMAGES

CROSS-REFERENCE TO RELATED APPLICATION

This application is a U.S. National Phase Application under 35 U.S.C. § 371 of International Application No. PCT/2016/036825, filed on Jun. 10, 2016, entitled "SYSTEMS AND METHODS FOR FINDING REGIONS OF INTEREST IN HEMATOXYLIN AND EOSIN (H&E) STAINED TISSUE IMAGES AND QUANTIFYING INTRATUMOR CELLULAR SPATIAL HETEROGENEITY IN MULTIPLEXED/HYPERPLEXED FLUORESCENCE TISSUE IMAGES," which claims the benefit of U.S. Provisional Application No. 62/174,197, filed on Jun. 11, 2015, entitled, "COMMON FRAMEWORK FOR FINDING REGIONS OF INTEREST IN HEMATOXYLIN AND EOSIN (H&E) STAINED TISSUE IMAGES AND QUANTIFYING INTRATUMOR CELLULAR SPATIAL HETEROGENEITY IN MULTIPLEXED/HYPERPLEXED FLUORESCENCE TISSUE IMAGES," the disclosures of which are incorporated herein their entirety.

BACKGROUND OF THE INVENTION

1. Field of the Invention

The present invention pertains to digital pathology, and in particular, to a common framework for finding regions of interest in hematoxylin and eosin (H&E) stained tissue images and for quantifying intratumor cellular spatial heterogeneity in multiplexed/hyperplexed fluorescence tissue images.

2. Description of the Related Art

Digital pathology refers to the acquisition, storage and display of histologically stained tissue samples and is initially gaining traction in niche applications such as: second-opinion telepathology, immunostain interpretation, and intraoperative telepathology. Typically, a large volume of patient data, consisting of 3-50 slides, is generated from biopsy samples and is visually evaluated by a pathologist, under a microscope, but with digital technology by viewing on a high-definition monitor. Because of the manual labor involved, the current workflow practices are time consuming, error-prone and subjective.

Cancer is a heterogeneous disease. In hematoxylin and eosin (H&E) stained tissue images, heterogeneity is characterized by the presence of various histological structures, such as carcinoma in situ, invasive carcinoma, adipose tissue, blood vessels, and normal ducts. One precision medicine approach to both intra- and inter-tumor heterogeneity is to sequence biopsied tissues and to identify a panel of disease-related genomic signatures, specifically for each patient and the distinct regions of a single patient's tumor. However, genomic/epigenomic profiling requires either crushing up tissues or taking multiple core samples from the tumor, yielding a time-consuming and low resolution understanding of the heterogeneity. Spatial interactions between the various histological structures can prognosticate the disease. For example, a tumor nest growing into (invading) blood vessels indicates an increased risk of metastasis. Accurate segmentation of histological structures can thus help build a spatial interaction map to facilitate precision medicine studies combining protein, DNA and RNA biomarkers for deep molecular profiling. This spatial interaction map can also serve as an exploratory tool for pathologists or as a guide to micro-dissection for further molecular profiling.

Histological structure segmentation is a very challenging task because structures such as normal ducts and carcinoma in situ have well-defined boundaries, but many others, such as invasive carcinoma and stroma, do not. Structural morphologies also vary significantly depending on tissue origins (e.g., breast vs. lung), and tissue preparation and staining practices. Historically, biomedical image analysis literature has focused on segmenting nuclei, since nuclei are building blocks for all higher level tissue structures. More recent methods have expanded to segmenting other histological structures, such as the glands in prostate and breast tissue images, with approaches based on nuclei-lumen association, region growth, region-based active contour in combination with Markov Random Field, and deep learning. Some other approaches involve engineering disease- and organ-specific extractors to facilitate analysis of publicly available datasets, such as MITOS (mitotic figures) and GlaS (glands). For example, a typical gland segmentation strategy may involve first identifying a lumen and then searching for the surrounding epithelial layer of cells. However, this strategy is unlikely to work in the case of breast carcinoma in situ, where the duct lumens may be completely filled by tumor cells. A basic mathematical foundation has been developed for supervised segmentation of H&E images, but that foundation has not been tested on more than a couple of examples.

Moreover, for many malignancies, molecular and cellular heterogeneity is a prominent feature among tumors from different patients, between different sites of neoplasia in a single patient, and within a single tumor. Intratumor heterogeneity involves phenotypically distinct cancer cell clonal subpopulations and other cell types that comprise the tumor microenvironment (TME). These cancer cell clonal subpopulations and other cell types include local and bone marrow derived stromal stem and progenitor cells, subclasses of immune inflammatory cells that are either tumor promoting or tumor-killing, cancer associated fibroblasts, endothelial cells and pericytes. The TME can be viewed as an evolving ecosystem where cancer cells engage in heterotypic interactions with these other cell types and use available resources to proliferate and survive. Consistent with this perspective, the spatial relationships among the cell types within the TME (i.e., spatial heterogeneity) appear to be one of the main drivers of disease progression and therapy resistance. Thus, it is imperative to define the spatial heterogeneity within the TME to properly diagnose the specific disease sub-type and identify the optimal course of therapy for individual patients.

To date, intratumor heterogeneity has been explored using three major approaches. The first approach is to take core samples from specific regions of tumors to measure population averages. Heterogeneity in the samples is measured by analyzing multiple cores within the tumor using a number of techniques, including whole exome sequencing, epigenetics, proteomics, and metabolomics. The second approach involves "single cell analyses" using the above methods, RNASeq, imaging or flow cytometry after separation of the cells from the tissue. The third approach uses the spatial resolution of light microscope imaging to maintain spatial context, and is coupled with molecular-specific labels to measure biomarkers in the cells in situ.

Spatial analysis using light microscope imaging facilitates analysis of large areas of tissue sections and/or multiple tumor microarray sections at the cellular and subcellular levels. Subcellular resolution, for example, permits the identification of the activation state of specific biomarkers (e.g. translocation of transcription factors into the nucleus). In addition, recent developments in mass spectrometry imaging permit many cellular constituents to be measured across a tissue section but at a lower resolution than optical microscopy.

Several light microscopy imaging platforms have been developed to characterize cellular biomarker expression levels within tumors including transmitted light and fluorescence. Multivariate information based on fluorescence has been acquired from images of large area tissue sections and tissue microarrays (TMAs) based on DNA, RNA and protein biomarkers, usually from 1 up to 7 fluorescently labeled biomarkers in the same sample (known as multiplexed fluorescence). Multiple commercial platforms can now be used to acquire, process, segment and perform some basic analysis of biomarker signal levels in tissue samples. Recently, platforms have been demonstrated that permit up to 60 fluorescently labeled antibodies and a few DNA or RNA hybridization probes to be acquired in an iterative cycle of labeling, imaging, and quenching fluorescence. It is also now possible to "map" the location of specific cell types, states of cell activations, cell biomarker expression levels and localizations, as well as extracellular constituents in tissue sections and TMAs.

A major challenge is to develop algorithms that can quantify key spatial relationships (interactions, and lack thereof) within the TME, based on panels of biomarkers. Initial efforts in measuring heterogeneity in tissue sections applied diversity metrics from ecological studies, such as Shannon entropy and Rao's quadratic entropy. However, these methods have not been adapted for multiplexed (up to 7 biomarkers) or hyperplexed (>7 biomarkers) immunofluorescence (IF) data. Other methods that account for high dimensional data may not have sophisticated cell phenotyping methods, allowing each biomarker to be only "on" or "off". Furthermore, few of these methods incorporate the spatial relationships between biomarker patterns in their heterogeneity scores. Indeed, the spatial organization of the TME has been hypothesized to be an important diagnostic biomarker in addition to the expression levels of selected biomarkers from cancer and non-cancer cells.

Other heterogeneity characterization methods have: (i) incorporated spatial information through region of interest sampling without using network-based approaches or taking advantage of multiplexed, (ii) analyzed linear relationships between biomarkers in multiplexed/hyperplexed IF data without considering nonlinear associations or spatial information, and (iii) have characterized multiplexed cell phenotype associations without any characterization of the underlying spatial organization within the tumor. In addition, most other methods report intra-tumor heterogeneity as a single score, thus potentially mapping two spatially different organizations of the TMEs incorrectly to the same score.

There is thus room for improvement in the fields of segmenting H&E images and quantifying intratumor cellular spatial heterogeneity in multiplexed/hyperplexed fluorescence tissue images.

SUMMARY OF THE INVENTION

In one embodiment, a method of identifying regions of interest in an H&E stained tissue image is provided. The method includes receiving image data representing the H&E stained tissue image, quantifying local spatial statistics for the H&E stained tissue image based on the received image data, identifying histological structures within the H&E stained tissue image based on the local spatial statistics, and generating a segmented H&E stained tissue image using the received image data and the identified histological structures.

In another embodiment, a non-transitory computer readable medium is provided that stores one or more programs, including instructions, which when executed by a computer, causes the computer to perform the method just described.

In yet another embodiment, a computerized system for identifying regions of interest in an H&E stained tissue image is provided. The system includes a processing apparatus, wherein the processing apparatus includes: (i) a quantifying component configured for quantifying local spatial statistics for the H&E stained tissue image based on received image data representing the H&E stained tissue image, (ii) an identifying component configured for identifying histological structures within the H&E stained tissue image based on the local spatial statistics, and (iii) a segmented tissue image generating component configured for generating a segmented H&E stained tissue image using the received image data and the identified histological structures.

In still another embodiment, a method of quantifying intratumor cellular spatial heterogeneity in fluorescence tissue images is provided. The method includes receiving image data representing a number of fluorescence tissue images, performing cellular segmentation on the received image data to identify a plurality of cells of the number of fluorescence tissue images, assigning each of the cells to one of a plurality of predetermined biomarker intensity patterns, quantifying spatial statistics for the number of fluorescence tissue images based on the assigned predetermined biomarker intensity patterns, and generating a visual representation of the quantified spatial statistics.

In another embodiment, a non-transitory computer readable medium is provided that stores one or more programs, including instructions, which when executed by a computer, causes the computer to perform the method just described.

In yet another embodiment, a computerized system for quantifying intratumor cellular spatial heterogeneity in fluorescence tissue images is provided. The system includes a processing apparatus, wherein the processing apparatus includes: (i) a cellular segmentation component configured for performing cellular segmentation on image data representing a number of fluorescence tissue images to identify a plurality of cells of the number of fluorescence tissue images, (ii) an assigning component configured for assigning each of the cells to one of a plurality of predetermined biomarker intensity patterns, (iii) a quantifying component for quantifying spatial statistics for the number of fluorescence tissue images based on the assigned predetermined biomarker intensity patterns, and (iv) a visual representation generating component for generating a visual representation of the quantified spatial statistics.

DETAILED DESCRIPTION OF EXEMPLARY EMBODIMENTS

Figure 1:
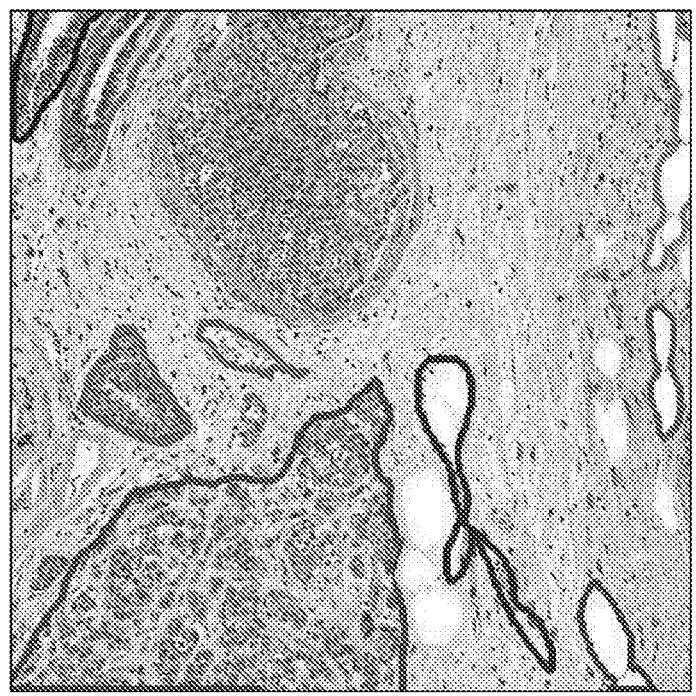
FIG. 1 is a sample H&E stained image.

As used herein, the singular form of "a", "an", and "the" include plural references unless the context clearly dictates otherwise.

As used herein, the statement that two or more parts or elements are "coupled" shall mean that the parts are joined or operate together either directly or indirectly, i.e., through one or more intermediate parts or elements, so long as a link occurs.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers. While certain ways of displaying information to users are shown and described herein with respect to certain figures or graphs as screen or screenshots, those skilled in the relevant art will recognize that various other alternatives can be employed. The screens or screenshots are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility. The screens or screenshots may also be printed as desired.

As used herein, the term "superpixel" shall mean a coherent patch or group of pixels with similar image statistics.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A. Segmenting H & E Stained Tissue Images

A first aspect of the disclosed concepts focuses on improving the function and operation of (e.g., with improved processing capabilities) digital pathology systems and, in particular, on segmenting histological structures in H&E stained images of tissues, such as breast tissues, e.g. invasive carcinoma, carcinoma in situ, atypical and normal ducts, adipose tissue, and/or lymphocytes. The present inventors hypothesized that spatial image statistics present discriminative fingerprints for segmenting a broad class of histological structures. This aspect of the disclosed concepts, described in greater detail herein, provides two graph-theoretic segmentation methods that each rely on characterizing local spatial statistics.

In the first method, each node in the graph corresponds to a pixel in the image, and the edges correspond to the strength with which two nodes belong to the same group. The edge strength is determined by measuring pairwise pixel statistics, in the form of bivariate von Mises mixture distributions, in an opponent color space built to enhance the separation between pink and purple stains in H&E images. Spectral methods are used to partition the graph. The first method is expected to be more successful in segmenting structures with well-defined boundaries (e.g., adipose tissues and blood vessels).

The second method is conveniently designed to extract histological structures that have amorphous spatial extent (e.g., a tumor nest). In this formulation, putative nuclei centers become the nodes of a graph formed to capture the spatial distribution of the nuclei in H&E images. By applying data-driven thresholds on inter-nuclei spatial distances, the network is partitioned into homogeneous image patches.

The two segmentation methods described herein have two common elements, namely opponent color representation and appearance normalization, each of which is described in detail below. The segmentation methods differ in how they capture image statistics and embed them into graph partitioning strategies. These aspects of the methods will be described separately herein.

Figure 2:
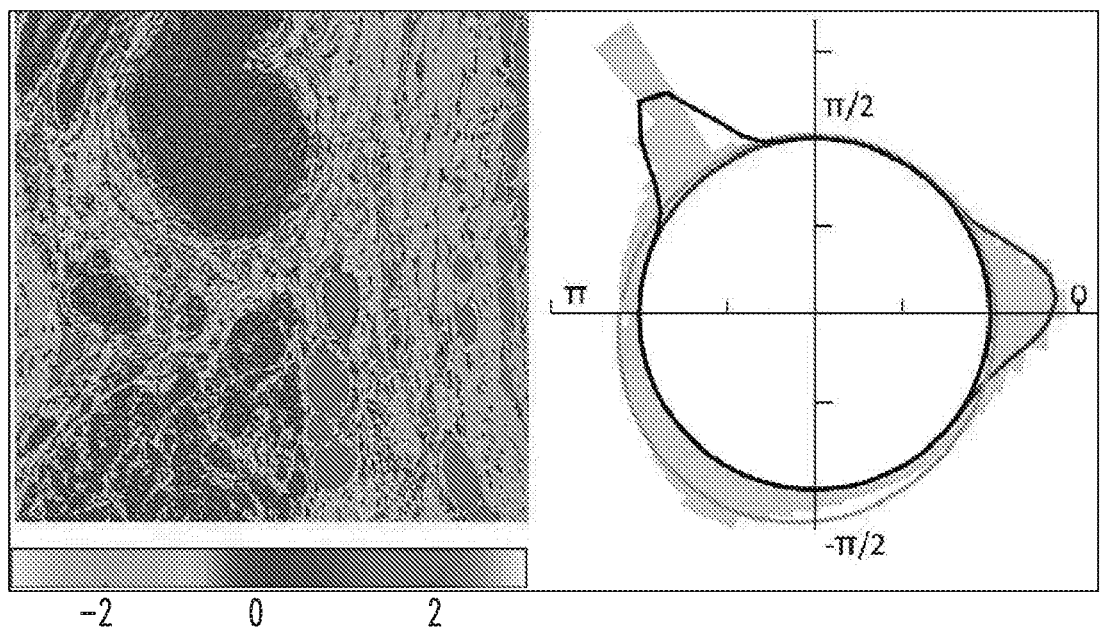
FIG. 2 shows the H&E image of FIG. 1 transformed into H&E hue space shown as a heat map (left) and an angular histogram (right)

When the known standard opponent-color (with red-green, yellow-blue as opponent color axes) hue-saturation-brightness (HSV) transformation is applied to red-green-blue (RGB) images from H&E, the pink and purple color ranges are restricted to the blue-red quadrant of the color wheel. A goal of this aspect of the disclosed concepts is to enhance the separation between pink and purple colors so that the downstream spatial analysis pipeline is more robust. For this, the construction of a color space is optimized to opponently place the pink and purple colors. Specifically, in the exemplary implementation, an expert was allowed to select a bag of pink and purple pixels. Then, singular value decomposition was performed on this collection of data to obtain an orthogonal projection matrix of size 3×3. This aspect of the disclosed concepts provides a specific interpretation to the projected coordinates, similar to the opponent space HSV. In particular, the projection onto the first singular vector (enforced to have non-negative values) yields an H&E-brightness value b. The two remaining projected coordinates, c2 and c3, form a complex plane in which H&E-saturation $s=\sqrt{c_2^2+c_3^2}$ and H&E-hue $\theta=\tan^{-1}(c_2+ic_3)$. From this construction, the hue values of purple and pink pixels are expected to be maximally separated in the complex color plane. For illustration, it is noted that the angular difference in the mean hue values of the pink and purple pixels in FIG. 1, which is a sample H&E stained image, is 1:7 radians, as shown in FIG. 2, which is the H&E image of FIG. 1 transformed into H&E hue space shown as a heat map (left) and an angular histogram (right). This spread is more than the value of ≈0:4 radians obtained from the standard HSV opponent color space. Hue value is unstable when the saturation is low. This is true for pixels mapped to the origin of the complex plane ($c_2$; $c_3 \approx 0$). In the standard HSV representation, all white pixels will have low saturation values and hence unstable hue angles. Note that white pixels can form a significant portion of an H&E image because of adipose tissue, lumen, tissue tears, and shrinkages. In the opponent color representation of this aspect of the disclosed concepts, by learning the rotation matrix from an expert-selected pink/purple pixel bag, white pixels are able to be given higher saturation values and more stable hue angles. However, there will be a population of pixels with low saturation values (say <0:005) that map to the origin of the complex plane. This population is empirically estimated to be around 0:3% for the H&E images of size 2K×2K that were used.

In addition, any inconsistencies in sectioning, staining, and imaging result in variation in color appearance of H&E images. Thus, in the exemplary embodiment, the data is normalized. Previous normalization methods have utilized stain vector estimation methods such as non-negative matrix factorization. These methods were found to be ineffective for this aspect of the disclosed concepts because the color distributions for some images are very skewed toward mostly purple or mostly pink. The present inventors hypothesized that the color appearance of two images is similar if their color statistics match. However, matching the statistics of the whole pixel population of the source and target images can result in unintended artifacts. For example, if the source image has mostly pink pixels (stroma) and the target image has mostly purple pixels (invasive carcinoma), then matching the source image statistics to the target image statistics will turn many pink pixels in the source image to purple and mistakenly change the cellular component identity of those pixels from stroma to nuclei. To address this issue, the following three classes of pixels are first identified: pink (eosin), purple (hematoxylin), and white (e.g., fat, shrinkage), and the statistics are matched separately for each of these classes. To identify the three classes, H&E images are converted into H&E-hue, H&E-saturation, and H&E-brightness channels as discussed. The H&E-hue space is angular and given the separation between pink, purple, and white pixel clouds in this space, the hue values are modeled with a mixture of univariate von Mises distributions. Univariate von Mises distribution for angular statistics is the equivalent counterpart of the univariate normal distribution for linear statistics. The von Mises distribution is characterized by two parameters, a mean $-\pi<\mu\leq\pi$ and a concentration parameter $\kappa>0$, and is given by: $f(x)=\{2\pi I_0(\kappa)\}^{-1} \exp \kappa \cos(x-\mu)$, where $I_0(\kappa)$ is the modified Bessel function of the first kind with order 0. A mixture of K univariate von Mises distributions is given by $\Sigma_{k=1}^{K} m_k f_k(x|\mu_k,\kappa_k)$, where $m_k$'s are the prior probabilities and $\mu_k$'s, $\kappa_k$'s are the means and concentration parameters. To explicitly account for pixels with low saturation values and unstable hue angles, a uniform angular noise is added as an additional mixture component whose prior probability is approximately 0.3%. The parameters of univariate von Mises mixture can be found using an expectation-maximization (EM) algorithm. The statistics of a distribution can be characterized by an infinite set of moments. However, for analytical convenience, in the exemplary embodiment, moments are computed only up to the fourth order (mean, standard deviation, skewness, kurtosis). In each channel, the moments of each pixel class from the source image are matched to the target image. For example, the moments of purple pixels in the source image are matched to the moments of purple pixels in the target image in all three channels. After normalizing the statistics in the H&E opponent color space, the resulting pixel values are converted into the RGB space (to create normalized RGB data) using the inverse of the rotation matrix described above.

Having described the two common elements of the two segmentation methods, namely opponent color representation and appearance normalization, the remainder of each segmentation method will now be described in detail. In each of the segmentation methods, normalized image data serves as inputs. In particular, normalized H&E-hue data is used as inputs in the first method, and normalized RGB data is used as inputs in the second method.

With regard to the first method, normal breast tissues have large areas of pink stained connective tissue (CT) surrounding small areas of ducts, each of which is an assembly of cells. The nuclei of these cells will be stained dark purple, while the cytoplasm that surrounds the nuclei exhibits a mixture of pink and purple, since the purple stain from the nuclei can spill over to the cytoplasm. Statistically speaking, if one were to stand on any of these nuclei, one would expect to be surrounded by purple pixels denoting the nuclei and pink-purple pixels denoting the cytoplasm. If these cells assemble into a duct structure, then in a given neighborhood of each cell, other cells exhibiting similar properties should be found. On the other hand, if one were stand on a fibroblast cell nucleus, which is found usually scattered in the connective tissue, one would find mostly pink pixels in its neighborhood. With the assumption that the statistical association within a structure such as ducts is higher than across its boundaries, ducts should be able to be segmented while ignoring the fibroblast cells scattered among the connective tissue.

Using a mixture univariate von Mises distributions, the image pixels can be separated into pink, purple and white classes, but this is insufficient to delineate histological structures, such as the glands/ducts, because such structures contain pixels from all three classes. In this aspect of the disclosed concepts, in order to segment these structures, it is assumed that the statistical association within a structure such as a duct is higher than across its boundaries, and this statistical association is modeled, according to this aspect of the disclosed concepts, using a mixture of bivariate von Mises distributions. Since the H&E-hue is an angular variable, the joint distribution P(A, B) of hue values from two neighboring pixels lies on a torus. This joint density is modeled as a mixture of bivariate von Mises distributions. Let the values of pixel A and B in H&E-hue space be $\varphi$ and $\psi$, respectively. The bivariate distribution of two angular variables, $-\pi<\varphi\leq\pi$ and $-\pi<\psi\leq\pi$ is:

$$f_c(\varphi,\psi)=C_c \exp[\kappa_1 \cos(\varphi-\mu)+\kappa_2 \cos(\psi-\nu)-\kappa_3 \cos(\varphi-\mu-\psi+\nu)]$$

where $\mu$, $\nu$ are the means and $\kappa_1$, $\kappa_2>0$ are the concentrations of $\varphi$, $\psi$, respectively, $\kappa 3$ is the correlation coefficient and $C_c$ is the normalizing constant. The full bivariate von Mises model has 8 parameters, but a reduced 5-parameter cosine model with positive interaction is used in the exemplary embodiment. The marginal density is: $f_c(\psi)=c_c 2\pi I_0(\kappa_{13})(\psi) \exp\{\kappa_2 \cos(\psi-\nu)\}$. The value of $\kappa_3$ decides whether the distribution is unimodal or bimodal. In particular, the joint density is unimodal if $\kappa_3<\kappa_1\kappa_2/(\kappa_1+\kappa_2)$ and it is bimodal if $\kappa_3>\kappa_1\kappa_2/(\kappa_1+\kappa_2)$ when $\kappa_1>\kappa_3>0$ and $\kappa_2>\kappa_3>0$.

When the values of neighboring pixels of the H&E image in the H&E-hue space are considered, there are at most six possibilities for the masses on the torus: purple-purple, pink-pink, white-white, and the three different pairwise interactions. To model this joint distribution, a mixture of six unimodal bivariate von Mises distributions is used. A mixture model of K bivariate von Mises distributions can be parameterized by: $f_c(\varphi,\psi)=\Sigma_{i=1}^K m_i f_i(\varphi,\psi|\mu_i,\nu_i,\kappa_{1i},\kappa_{2i},\kappa_{3i})$. The initial values of $\mu_i$, $\nu_i$, $\kappa_{1i}$, and $\kappa_{2i}$ are generated from the mixture of univariate von Mises for all the pixels in the image. The concentration parameters $\kappa_{1i}$, and $\kappa_{2i}$ and the correlation parameter $\kappa_{3i}$ satisfy the unimodality conditions for $f_i$. $\kappa_{3i}$ is constrained to have values between $-1$ and $1$ to avoid distortion to the elliptical patterns (observed in sampled data). Together with the above constraints, the parameters of the mixture are estimated by an EM algorithm. Since there are at most six components of the mixture model as reasoned above, an explicit model selection step is not undertaken for the mixture model. If the H&E image lacks any one of the three basic colors, purple, pink, and white, the prior probabilities or mixing proportions of clusters related to that color will be close to 0.

Consider modeling the statistical dependencies between hue angles of neighboring pixels in the H&E opponent color space. If the joint probabilities are used as a measure of statistical association, it may be found that the pink-pink pixel pair in the connective tissue has a higher probability than a purple-purple pixel pair inside a duct or a pink-purple pixel pair across the CT-duct boundary. However, because of the overabundance of pink in some H&E images, the combination of pink-purple pixel pairs across the CT-duct boundary may have an equivalent or even higher probability than a purple-purple pixel pair inside the duct. A pink-pink pair may have the highest joint probability and a purple-purple pair may have similar joint probability to a purple-pink pair. In other words, the joint probability might not be sufficient to detect correct boundaries. This can be improved by the use of mutual information (MI) to correct for relative abundance. To compute MI, a number of pixel pairs (A,B) with features $\vec{f_A}$ and $\vec{f_B}$ (e.g. H&E-hue angles) are selected randomly from all locations of the image and with distances less than a threshold. The joint probability of features of A and B at a distance d apart is denoted as p(A, B; d). The overall joint probability is defined as:

$$P(A, B) = \frac{1}{Z}\sum_{d=d_0}^{\infty} w(d) p(A, B; d).$$

The value of d depends on the parameter $\sigma$, in particular $d=2+2|r|$ where $r\sim N(0, \sigma)$. A nucleus is $\approx 15$ pixel in diameter at 10× magnification. Since the segmentation algorithm targets assembly of nuclei, the distances between pixel pairs sampled should cover at least the diameter of a nucleus. Hence, $\sigma$ is set to 3. The pointwise mutual information (PMI) is calculated from the joint probability P(A,B) modeled by a mixture of bivariate von Mises distribution and the marginal probabilities P(A) and P(B) modeled by a mixture of univariate von Mises distributions. In particular, $$PMI_\rho(A, B) = \log\frac{P(A, B)^\rho}{P(A)P(B)}.$$

In the exemplary embodiment, $\rho=2$ to normalize for the upper bound of $$\frac{P(A, B)^\rho}{P(A)P(B)}.$$

Furthermore, an affinity function is defined from PMI to indicate the likelihood of grouping two pixels into the same histological structure. The affinity matrix W with elements $w_{i,j}$ denotes similarity between pixels i and j:

$$w_{i,j} = e^{PMI_\rho(\vec{f_i},\vec{f_j})}.$$

The affinity function is used as an input to a standard spectral graph segmentation method, such as that described in Arbelaez, P. et al., "Contour Detection and Hierarchical Image Segmentation", IEEE TPAMI, 33(5), 898-916 (20122) that has been the state-of-the-art for segmenting natural images. From the affinity matrix W, eigenpairs $\vec{v},\lambda$ of the generalized system are found: $(D-W)\vec{v}=\lambda D\vec{v}$. Dominant eigenvector maps (small eigenvalues) indicate boundary locations of potential histological structures. As is well known, no single eigenvector will be capable of capturing all possible boundaries in complex images. Hence, the usual practice is to calculate an edge strength map from oriented spatial derivative of a large number of dominant eigenvectors. A post-processing step is used to eliminate spurious boundary pixels.

Figure 3:
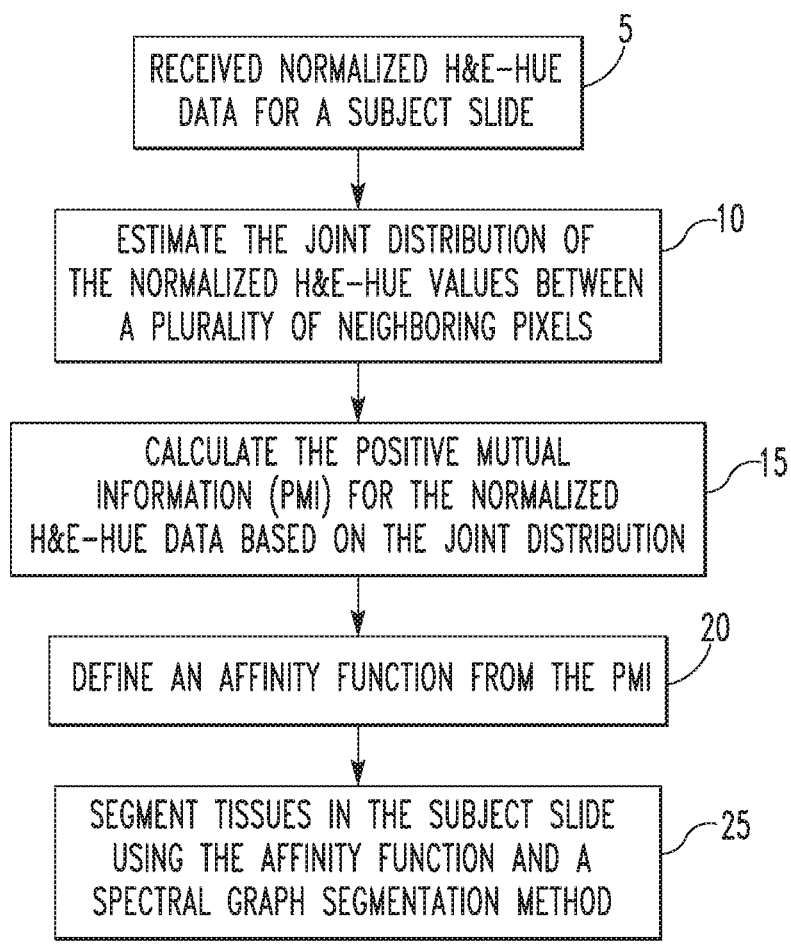
FIG. 3 is a flowchart showing a first segmentation method according to an aspect of the disclosed concepts.

FIG. 3 is a flowchart that summarizes the first segmentation method as just described in detail. The method begins at step 5, wherein normalized H&E-hue data for a subject slide is received. Next, at step 10, the joint distribution of the normalized H&E-hue values between a plurality of neighboring pixels in the H&E-hue data is estimated. Then, at step 15, the PMI for the normalized H&E-hue data is calculated based on the estimated joint distribution. At step 20, an affinity function is defined from the calculated PMI. Finally, at step 25, tissues in the subject slide are segmented using the affinity function and a spectral graph segmentation method (also known as spectral clustering).

With regard to the second segmentation method, local spatial statistics vary between the various histological structures in breast tissues. For example, the clump of cells in ductal carcinoma in situ tends to aggregate with their boundaries in close proximity of each other, because the in situ tumor is growing but is confined within ducts. On the other hand, epithelial cells in invasive carcinoma are spatially far apart. They are also growing, but can freely infiltrate into and through the breast stroma, no longer confined to ducts. Local statistics of normal ducts is more ordered, in particular, normal epithelial (inner) and myoepithelial cells (outer) form two layers surrounding a cavity (lumen).

For adipose tissue, the nuclei are small and to one side of the cells. The majority of adipose tissue consists of fat droplets. The present inventors hypothesized that different histological structures have different distributions of inter-nuclei distances (local statistics). As described below, the second segmentation method of this aspect of the disclosed concepts is based on this hypothesis.

Nuclei segmentation in histopathological and cytopathological images is an extensively researched problem. However, the close proximity of epithelial cells and the prevalence of mitotic figures (dividing cells) in breast cancer make it difficult to accurately detect nuclear boundaries, which is even difficult for human eye. To avoid this issue, in the second segmentation method, putative nuclei locations are identified in the form of superpixels, which will approximately represent nuclei, and a graph connecting superpixels is constructed to obtain neighborhood and distance information for each superpixel pair. More specifically, in the exemplary embodiment, in order to generate superpixels from H&E images, first, the pixel colors are normalized as described above. Then, the algorithm proposed in Tosun, A. B. and Gunduz-Demir, C., "Graph Run-length Matrices for Histopathological Image Segmentation", IEEE TMI, 30(3), 721-732 (2011), is performed to fit circular shaped superpixels. Briefly, this algorithm first clusters pixels into three classes based on intensities using k-means algorithm, in which cluster centers are determined over randomly selected training images using principal component analysis. These three classes represents purple, pink, and white regions which correspond to nuclei, stroma and lumen/white regions respectively. This algorithm then fits circular superpixels into clustered pixels for nuclei, stroma and lumen/white components. After superpixel decomposition, a Delaunay triangulation is formed based on center coordinates of superpixels to determine the neighborhood of each superpixel. Having the distance information for each superpixel pair, final segmentation of histological structures is achieved by partitioning this graph in a greedy manner and applying merging rules for specific types of segments, which is detailed in following sections. Although the proposed method is motivated by the inter-nuclei distance distribution, superpixels pairs from both purple and white pixel classes are considered to account for complex histological structures such as ducts, blood vessels and adipose tissues. For example, normal duct has purple nuclei forming two cell layers surrounding a white lumen area. On the other hand, the stroma (pink) class is considered as the background and is not included in graph partitioning step.

More specifically, each superpixel is considered a node in a graph and the connectivity of the graph is determined by a distance threshold. For each class, the pairwise distance between a superpixel center and its nearest 15 neighbors (identified by the Delaunay triangulation) is calculated. The distance threshold $\tau$ is set to be proportional to the median value ($\delta$) of the distance distribution. The proportionality constant is set to maximize the performance of the algorithm for the entire database. After building the superpixel graph, a greedy connected component analysis algorithm is used to cluster superpixels into labeled segments. In the exemplary embodiment, the largest 15 segments in terms of tissue area are selected. Since tissue images in the exemplary embodiment are of size 2K×2K, only a handful of ducts, tumor nests, fat droplets are expected in any given image. At this point, two sets of labeled segments have been obtained from the purple and the white superpixels.

To merge purple segments and white segments into the final histological structures, a few simple rules are followed to make sure that important structures formed by nuclei clusters are not missed. If a white segment is completely covered by a purple segment, the whole purple area takes the label of the purple segment. If a white segment overlaps with a purple segment, regardless of overlapping area, the overlapping part takes the label of the purple segment and the non-overlapping part takes the label of the white segment. If a purple segment is completely covered by a white segment, the purple area takes the purple segment's label and the remaining white area retains the white segment's label. This is to make sure that a nuclei clump residing within a vessel is not missed. After merging purple and white segments, the remaining unlabeled area is considered as background or stroma.

Figure 4:
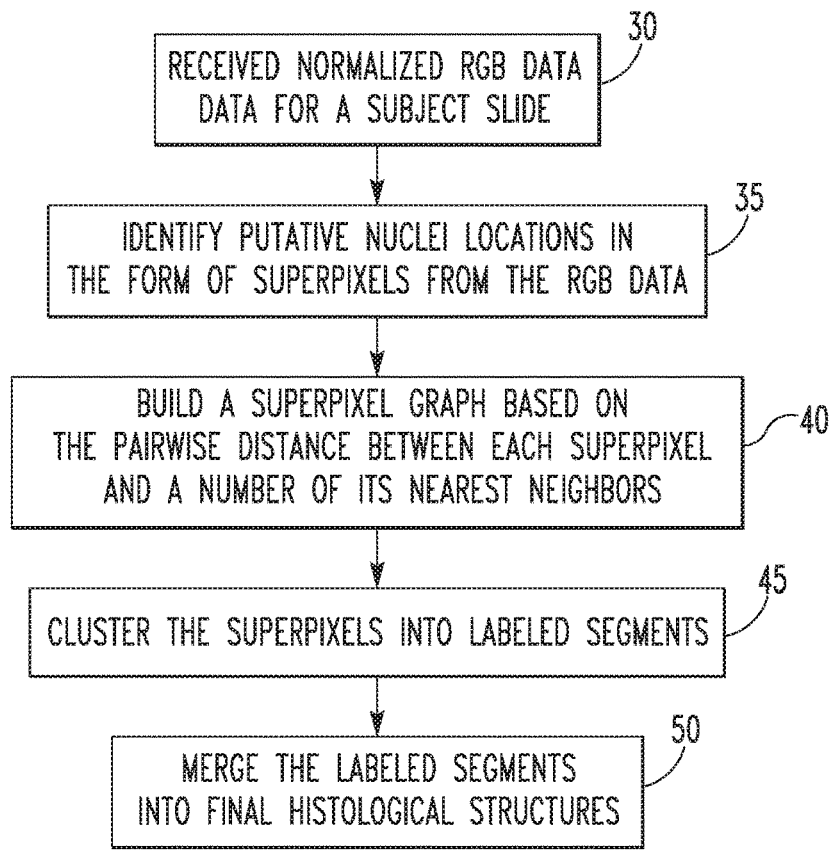
FIG. 4 is a flowchart showing a second segmentation method according to an aspect of the disclosed concepts.

FIG. 4 is a flowchart that summarizes the second segmentation method as just described in detail. The method begins at step 30, wherein normalized RGB data for a subject slide is received. Next, at step 35, putative nuclei locations are identified in the form of superpixels from the RGB data. Then, at step 40, a superpixel graph is built based on the pairwise distance between each superpixel and a number of its nearest neighbors. Next, at step 45, using the superpixel graph, the superpixels are clustered or grouped into labeled segments. Finally, at step 50, the labeled segments are merged into final histological structures. The determined final histological structures are then used to segment the subject slide (i.e., create an image wherein the subject slide is segmented).

B. Quantifying Intratumor Spatial Heterogeneity

As described in greater detail herein, another aspect of the disclosed concepts provides improvements in the function and operation of (e.g., improved processing) digital pathology systems. In particular, this aspect provides a method for quantifying intratumor spatial heterogeneity that can work with single biomarker, multiplexed, or hyperplexed immunofluorescence (IF) data. The method is holistic in its approach, using both the expression and spatial information of an entire tumor tissue section and/or spot in a TMA to characterize spatial associations. In the exemplary embodiment described in detail herein, the method generates a two-dimensional heterogeneity map to explicitly elucidate spatial associations of both major and minor sub-populations. It is believed that the characterization of intratumor spatial heterogeneity will be an important diagnostic biomarker for cancer progression, proliferation, and response to therapy, and thus the method and system of this aspect of the disclosed concepts will be a valuable diagnostic and treatment tool.

According to this aspect of the disclosed concepts, a predetermined set of particular biomarkers is employed to quantify spatial heterogeneity in multiplexed/hyperplexed fluorescence tissue images. For illustrative purposes, this aspect of the disclosed concepts is demonstrated herein in a non-limiting exemplary embodiment wherein spatial heterogeneity is quantified using three breast cancer biomarkers (estrogen receptor (ER), human epidermal growth factor 2 (HER2), and progesterone receptor (PR)) combined with biomarkers for segmentation including the nucleus, plasma membrane, cytoplasm and epithelial cells. It will be understood, however, that this aspect of the disclosed concepts may be used with different and/or additional biomarkers. In addition, it will also be understood that the impact of this aspect of the disclosed concepts, which uses pointwise mutual information (PMI) to quantify spatial intratumor heterogeneity, can be extended beyond the particular exemplary embodiments described herein. For example, and without limitation, this aspect of the disclosed concepts may be extended to the analysis of whole-slide IF images, labeled with increasing numbers of cancer and stromal biomarkers.

Furthermore, this aspect of the disclosed concepts employs a predetermined set of dominant biomarker intensity patterns (based on the predetermined set of particular biomarkers being used), also referred to herein as phenotypes, to measure and quantify cellular spatial heterogeneity. Thus, as an initial matter, a non-limiting exemplary method of establishing the set of dominant biomarker intensity patterns will first be described below with reference to FIG. 5. Thereafter, the manner in which the set of dominant biomarker intensity patterns is employed to quantify spatial heterogeneity is described.

Figure 5:
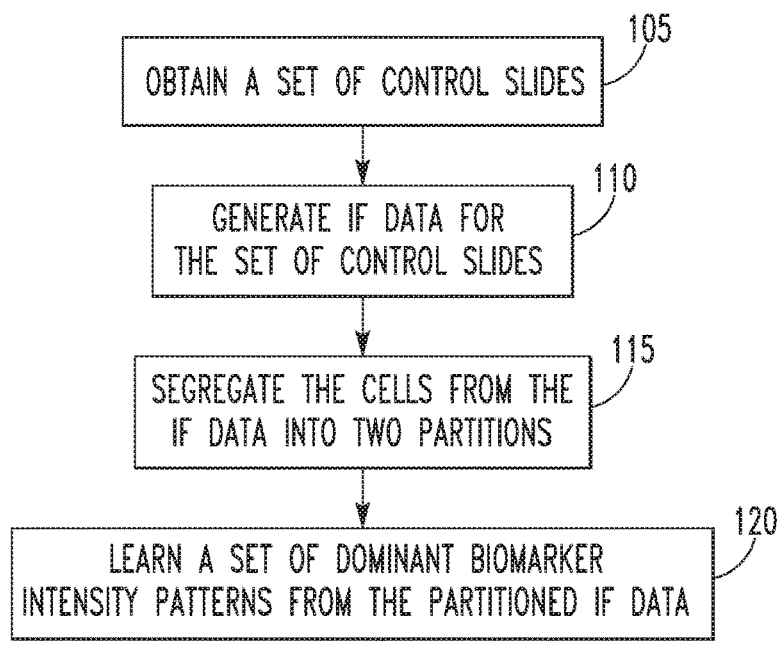
FIG. 5 is a flowchart showing a method of establishing a set of dominant biomarker intensity patterns according to an aspect of the disclosed concepts.

Referring to FIG. 5, first, at step 105, a set of digital control slides is obtained wherein each control slide includes a digital biomarker image which has been cell segmented (i.e., a cell segmentation method has been performed thereon). In the exemplary embodiment described herein for illustrative purposes, at least the three biomarkers described above (ER, PR and HER2) were used in the generation of the biomarker images of the control slides. Next, at step 110, immunofluorescence (IF) data is generated for the set of control slides. In particular, the IF data is generated in step 110 by obtaining, for each biomarker image, the intensity level of each of the predetermined biomarkers for each segmented cell in the biomarker image. Thus, as will be appreciated, the IF data will comprise biomarker intensity level data for each segmented cell of each biomarker image of the control slides.

Figure 6:
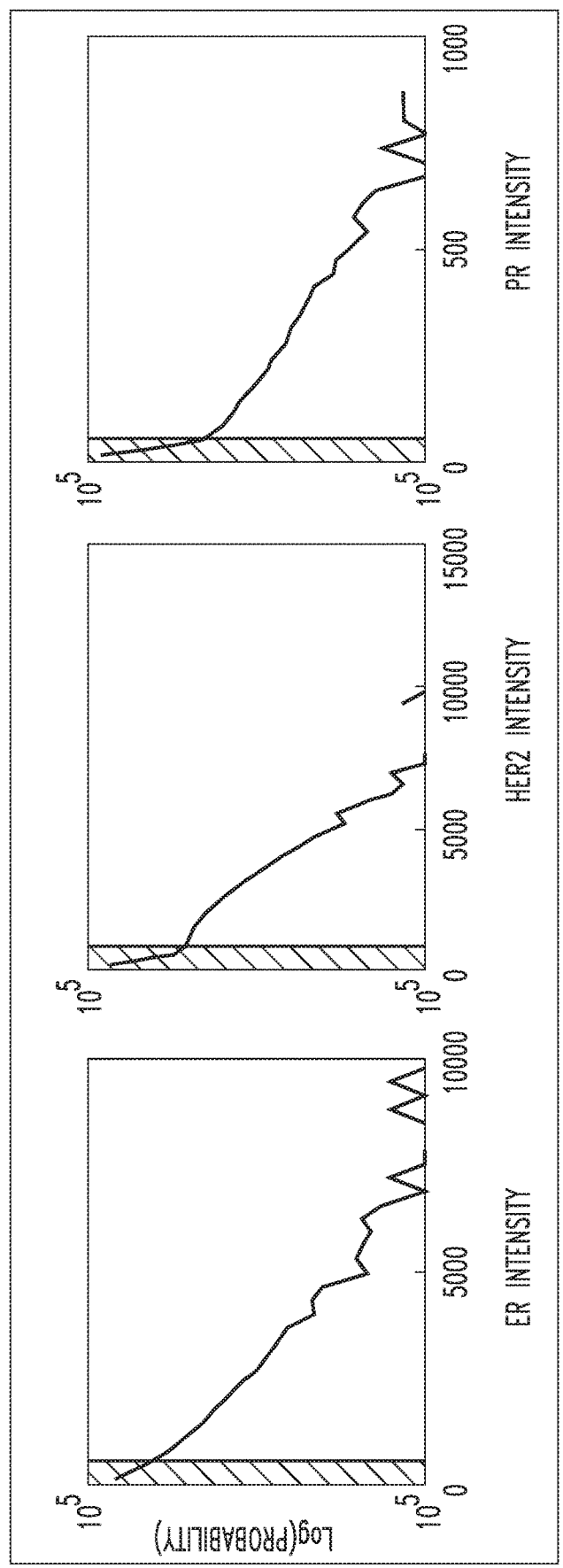
FIG. 6 shows biomarker intensity distribution graphs with vertical lines drawn to show two different regimes L1 and L2 for exemplary biomarkers employed in the method described herein.

Next, at step 115, the cells from the IF data are segregated into two partitions (using thresholds as described below) based on the distribution of signal intensity for each biomarker, under the assumption that signal intensity indicates true biomarker expression. FIG. 6 shows biomarker intensity distribution graphs for each of the exemplary biomarkers (ER, PR, HER2). Each of the log-occurrence distributions shown in FIG. 6 may be modeled by two or more linear equations. The notch where these two different models would meet is set to be the threshold for that particular biomarker channel, and is drawn as vertical lines in the biomarker intensity distribution graphs of FIG. 6. For any given cell, if one or more of its biomarker intensities is above threshold, that cell is classified as level 1 (L1). If all of the biomarker intensities for any given cell are below the thresholds in their corresponding biomarker channels, that cell is classified as level 2 (L2). These two partitions can be interpreted in terms of their signal-to-noise ratio, where L1 has a higher signal-to-noise ratio and L2 has a lower signal-to-noise ratio, in comparison. Each partition of cells is used to learn its own set of biomarker intensity patterns. This approach seems particularly judicious, given that the distribution of pattern coefficients for L1 and L2 data have different Gaussianity in general. As shown in FIG. 6, the studied biomarker intensities have long-tailed distributions, so a log-intensity representation is chosen to derive a numerically stable pattern recognition algorithm.

Figure 7:
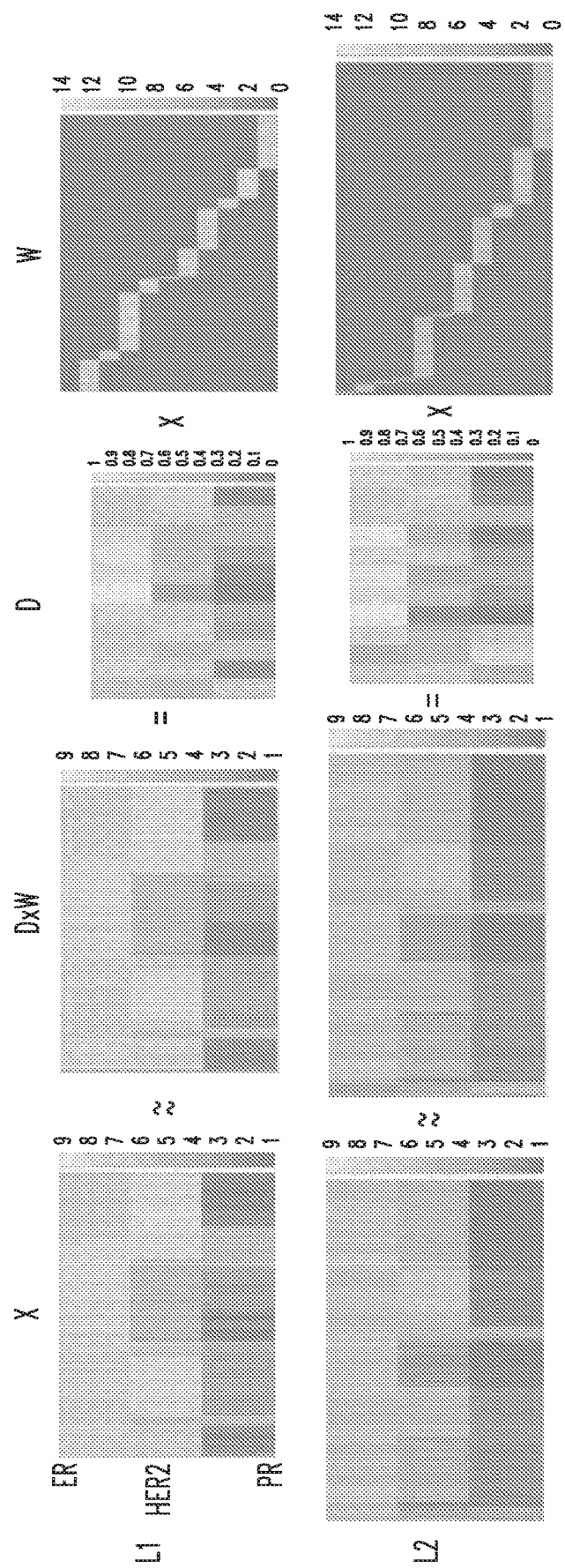
FIG. 7 shows pattern dictionaries learned separately for the two biomarker intensity regimes L1 and L2 shown in FIG. 6.
Figure 8:
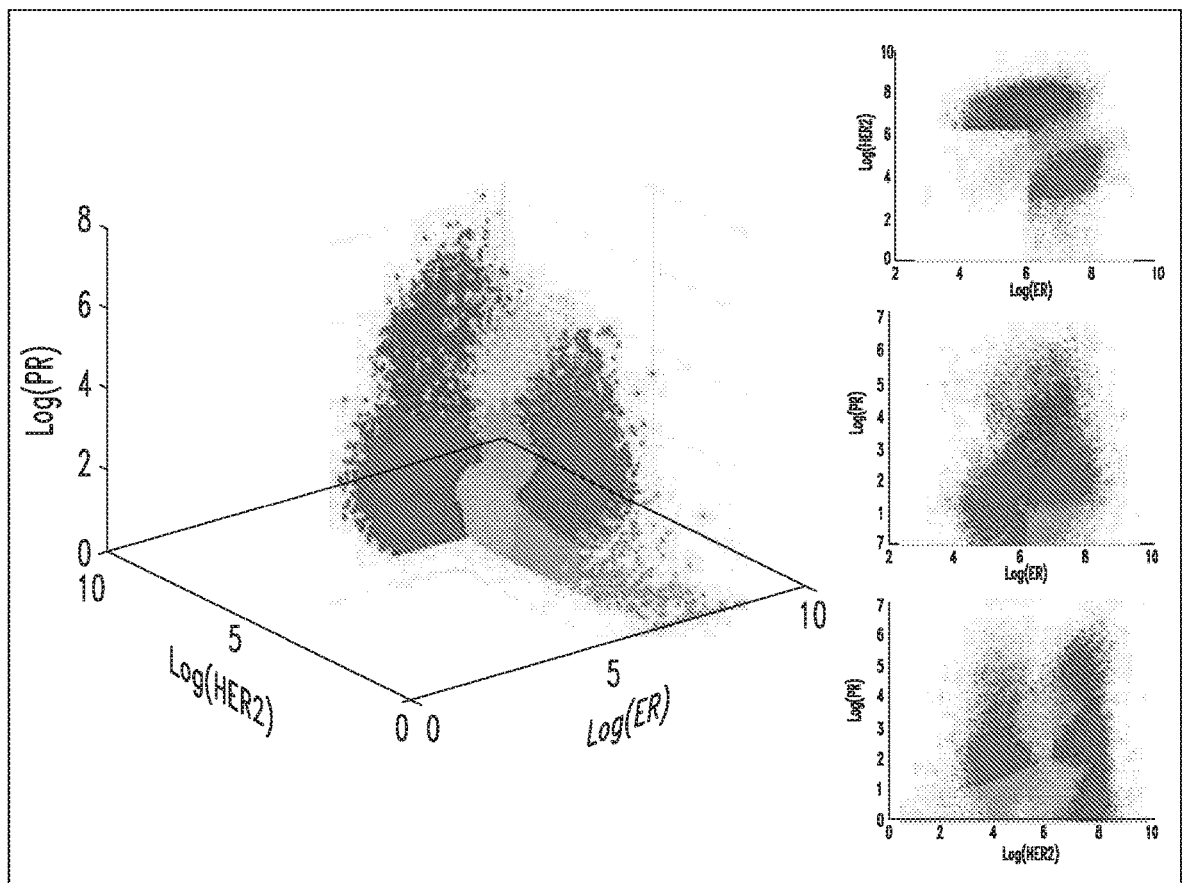
FIG. 8 shows a 3D representation of the biomarker data from the cellular population in the L1 regime with each cell phenotyped to belong to one, and only one, pattern in the dictionary and thus shown in a distinct color.

Next, at step 120 of FIG. 5, a set of dominant biomarker intensity patterns, also referred to herein as phenotypes, is learned from the partitioned IF data as follows. First, for each partition of the IF data, L1 and L2, a sparse signal representation is derived as seen in FIG. 7. More specifically, referring to FIG. 7, a given data matrix X, where the columns represent each cell in the IF data, and the rows represent the log biomarker intensities of each cell (top to bottom, ER, HER2, PR, respectively), can be approximated by the product of matrices D and W. D represents a dictionary of potential biomarker intensity patterns learned from the ensemble of cells in the dataset X, where each column represents one of the patterns learned from the data, and each row represents the respective biomarker intensities of each pattern. W is a sparse matrix, which phenotypes each cell in X to a specific pattern in D with a particular scaling coefficient. Thus, each cell (column in W) is represented by only one cell phenotype, which corresponds to the biomarker pattern (column in D) where the sparse code lies. The color spectrum for each matrix varies from one color, for example blue (low intensity) to another color, for example yellow (high intensity). Matrix DW is displayed to portray the similarity between the actual data matrix and its reconstruction. By viewing matrices X and DW, which are column sorted by the dictionary element they have the most consensus with, it can be observed that each of the biomarker intensity patterns is present in the data. The benefit of this reconstruction of the data is the ability to represent a large array of cell-level data with a small number of interpretable biomarker intensity patterns, describing highly clustered clouds inherent to the dataset as shown in FIG. 8. Each cell in the 3D log biomarker intensity space is color coded by its phenotype. The reconstruction error of the linear representation of a given dataset X into dictionary D and dictionary coefficient matrix W is highly dependent on the dimensionality of D, i.e., the number of patterns that will be used to describe the dataset X.

Figure 9:
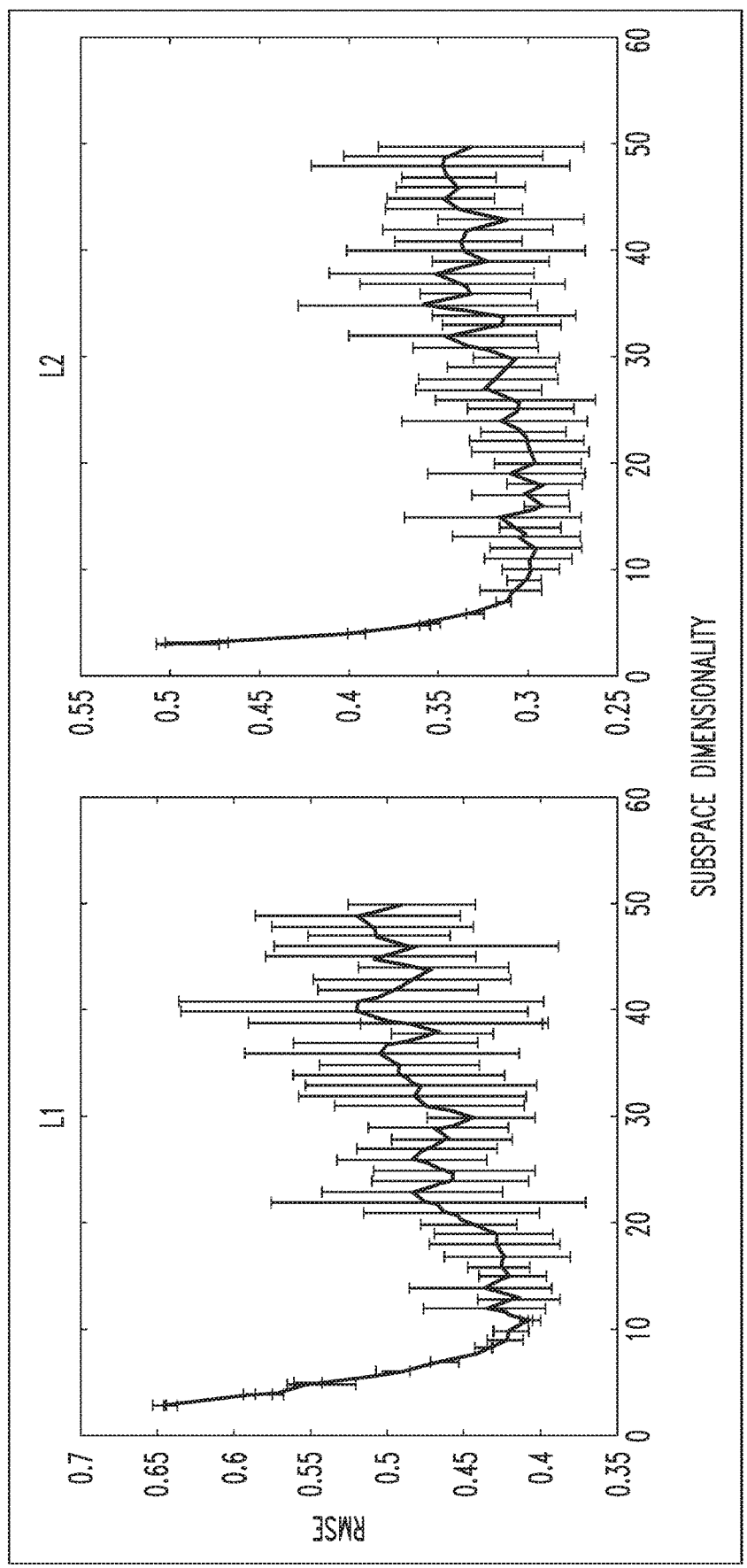
FIG. 9 illustrates the determination of the optimal size of the pattern dictionaries for biomarker intensity regimes L1 and L2.
Figure 10:
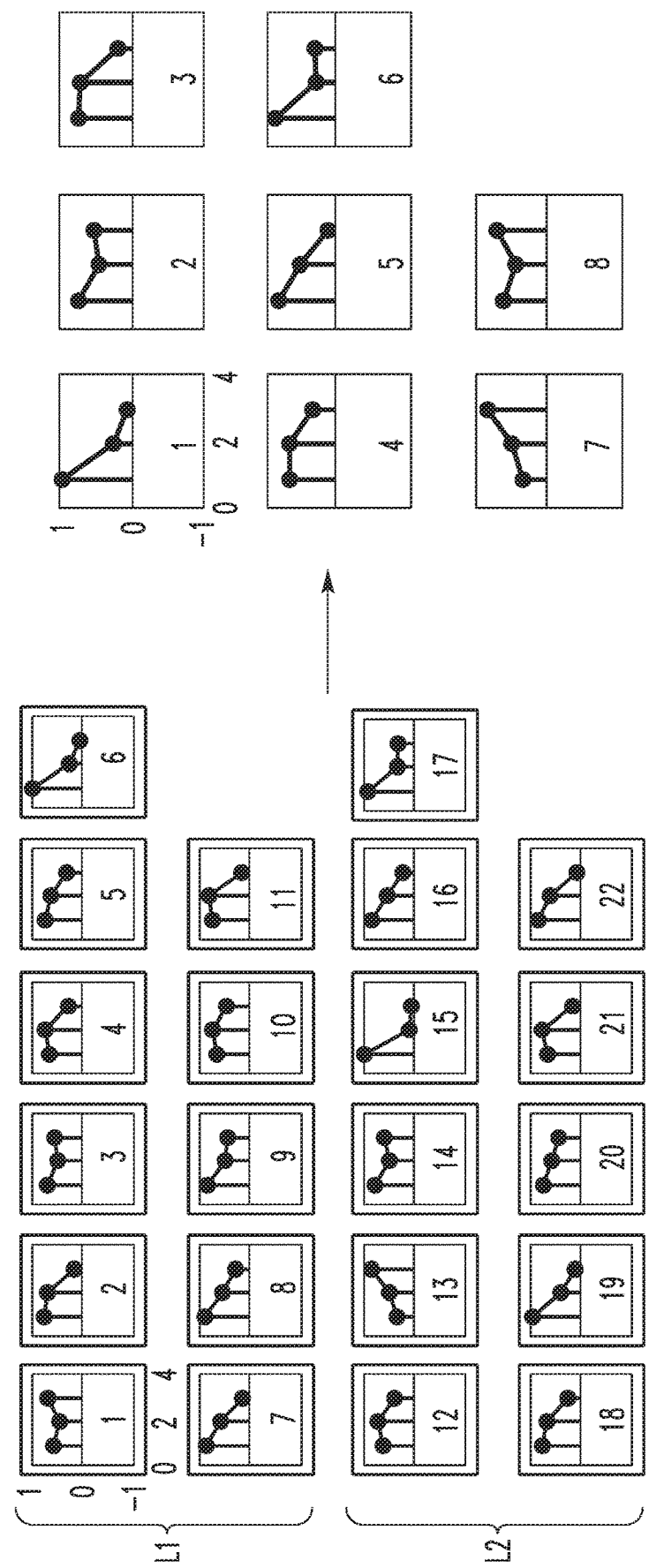
FIG. 10 illustrates consolidating the pattern dictionaries of regimes L1 and L2 into one.

In order to choose the ideal dimensionality of D, a ten-fold cross validation of the data reconstruction is performed as shown in FIG. 9. As is typical in these analyses, it is noted that as the dimensionality increases, reconstruction error and the variance of the error decrease, until a certain point where the error variance begins to increase with dimensionality. In the exemplary embodiment, it has been found that a dictionary size of 11 patterns optimizes both reconstruction error and variance of the error, for both data partitions, L1 and L2. Having learned a set of 11 patterns for each non-overlapping partition of the data L1 and L2, the two dictionaries could be merged into a large single dictionary of biomarker intensity patterns that can describe the entire dataset. However, since these patterns were learned separately from partitions deriving from the same dataset, captured under the same experimental conditions, it was noted that there were some redundancies between the dictionary learned from L1 data and the dictionary learned from L2 data. Thus, in the exemplary embodiment, k-means clustering was used to consolidate the large 22 pattern dictionary (with 11 patterns from each partition) into a smaller final dictionary containing only the unique patterns discovered from approach described herein. FIG. 10 shows the 11 patterns learned from L1 and the 11 patterns learned from L2. Each biomarker pattern is represented as a stem plot of its ER, HER2, and PR intensity, respectively. For convenience, the intensity patterns in the stem plots will be described as being high, medium, and low. For example, pattern 8 in the L1 dictionary (shown to the left) may be described as ER high, HER2 medium, and PR low.

The results of k-means clustering, shown to the right in FIG. 10, result in a final dictionary dimensionality of 8 biomarker intensity patterns. In the exemplary embodiment, the final dimensionality was chosen based on the results of a silhouette criterion for clustering evaluation. Note that one pattern was unique to partition L2, pattern 7 of the final pattern set, with low ER expression, intermediate HER2 expression, and high PR expression. This demonstrates the value of partitioning the data into two groups, L1 and L2, where patterns dominant in one partition, but not the other, may be elucidated.

Having described the exemplary methodology for learning a set of dominant biomarker intensity patterns, the discussion will now shift to the manner in which the set of dominant biomarker intensity patterns is employed to quantify spatial heterogeneity. In particular, FIG. 11 is a flowchart showing the steps of a method for quantifying spatial heterogeneity of multiplexed/high perplexed fluorescence tissue images according to an exemplary embodiment.

Figure 11:
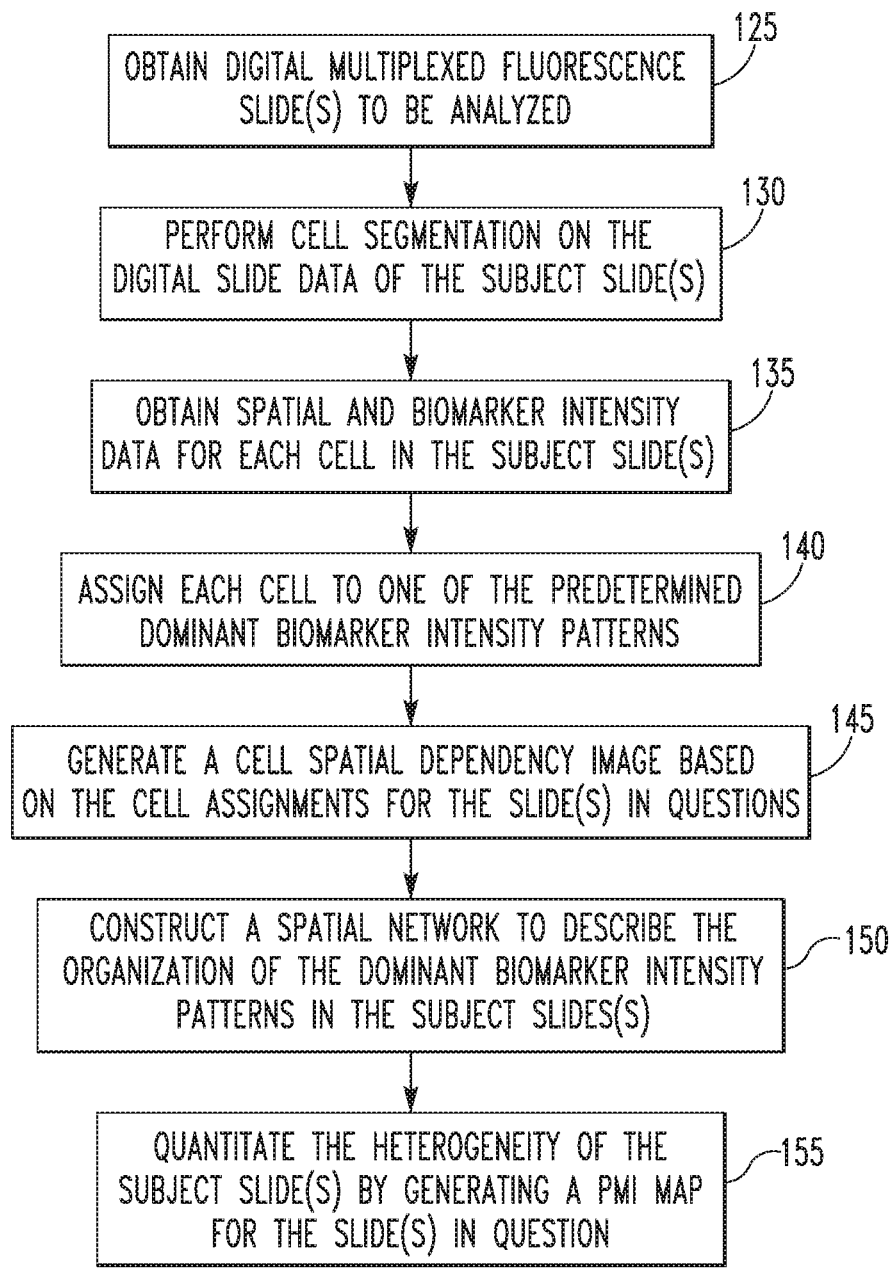
FIG. 11 is a flowchart showing the steps of a method for quantifying spatial heterogeneity of multiplexed/high perplexed fluorescence tissue images according to an exemplary embodiment.
Figure 12:
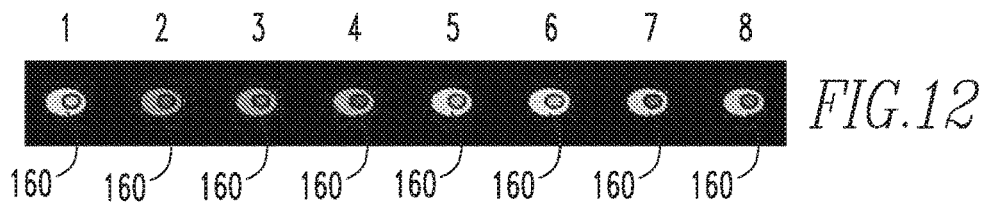
FIG. 12 shows a schematic representation the predetermined dominant biomarker intensity patterns employed according to an exemplary embodiment.
Figure 13:
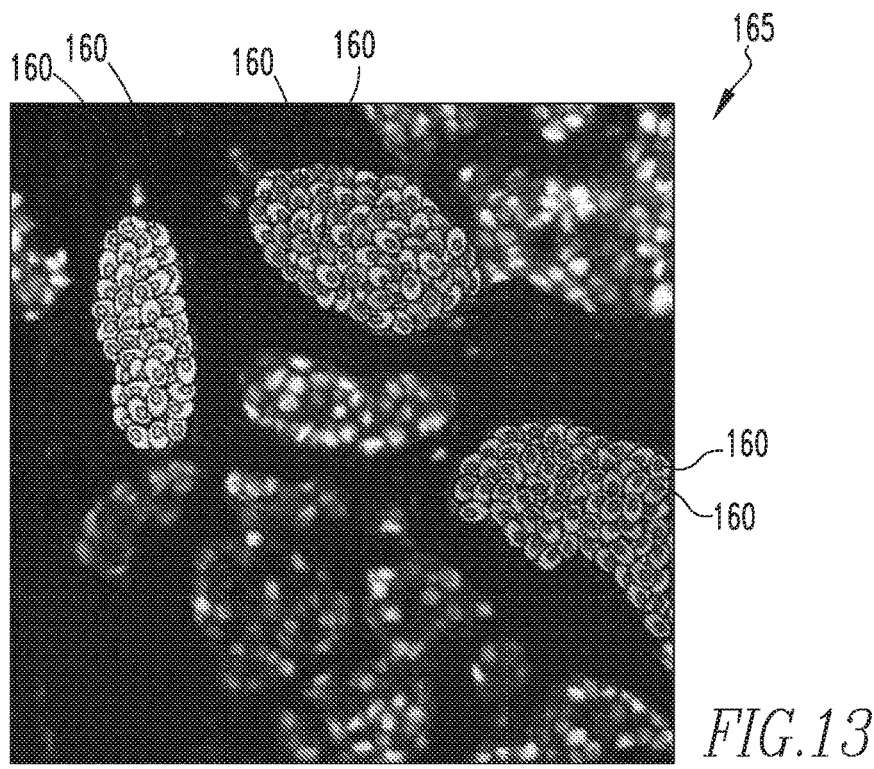
FIG. 13 shows a cell spatial dependency image according to an exemplary embodiment.

Referring to FIG. 11, the method begins at step 125, wherein a number digital multiplexed fluorescence slides to be analyzed is obtained. The number of slides obtained in step 125 may be a single slide, multiple slides from a single patient, or multiple slides for an entire patient cohort. As will be appreciated, the slide(s) obtained in step 125 will each include a section of a tumor of interest, and will each be a biomarker image of that section. As noted elsewhere herein, the biomarkers being used in the exemplary embodiment are ER, PR, and HER2. Next, at step 130, cell segmentation is performed on the digital slide data of the subject slide(s). Any of a number of known or hereafter developed suitable cell segmentation algorithms may be employed at step 130. Then, at step 135, spatial location and biomarker intensity data for each cell in the subject slide(s) is obtained. Next, at step 140, each cell of the subject slide(s) is assigned to one of the predetermined dominant biomarker intensity patterns (i.e., one of the phenotypes) based on the biomarker intensity composition of the cell. FIG. 12 shows a schematic representation 160 of each of the predetermined dominant biomarker intensity patterns, labeled 1-8. In the exemplary embodiment, each schematic representation 160 is provided in a unique color or colors so as to enable the schematic representations to be readily distinguishable from one another. Next, at step 145, the cell assignments and the schematic representations shown in FIG. 12 are used to generate a cell spatial dependency image which visually demonstrates the heterogeneity of the subject tissue sample(s). FIG. 13 shows a cell spatial dependency image 165 according to one particular exemplary embodiment of the disclosed concept. As seen in FIG. 13, cell spatial dependency image 165 shows spatial dependencies among the cells of the subject slide(s) using the schematic representations 160. In the exemplary embodiment, cell spatial dependency image 165 records the probabilities of the following cases: (i) if immune cells occur in the vicinity of cancer cells, (ii) if immune cells and cancer cells suppress each other, and (iii) if immune cells and cancer cells are agnostic of each other. Cell spatial dependency image 165 is not meant to show any particular tissue structure.

Next, at step 150, a spatial network is constructed to describe the organization of the dominant biomarker intensity patterns in the subject slide(s). Then, at step 155, the heterogeneity of the subject slide (s) is quantitated by generating a PMI map for the slide(s) as described herein. In the exemplary embodiment, steps 150 and 155 are performed as set forth below.

In order to represent the spatial organization of the biomarker patterns in the biomarker image (i.e., the tissue/tumor sample) of the subject slide(s), a network is constructed for the subject slide(s). The construction of spatial networks for tumor samples intrinsically couples cellular biomarker intensity data (in the nodes of the network) to spatial data (in the edges of the network). The assumptions in the network construction are that cells have the ability to communicate with nearby cells up to a certain limit, e.g., up to 250 µm, and that the ability for cells to communicate within that limit is dependent upon cellular distance. Therefore, the probability distribution in the exemplary embodiment is computed for the distance between a cell in the subject slide and its 10-nearest neighbors. A hard limit was chosen based on the median value of this distribution times 1.5 (to estimate the standard deviation), where cells in the network were connected only within this limit. Then, the edges between cells in the network are weighted by the distance between the adjacent cells.

Figure 14:
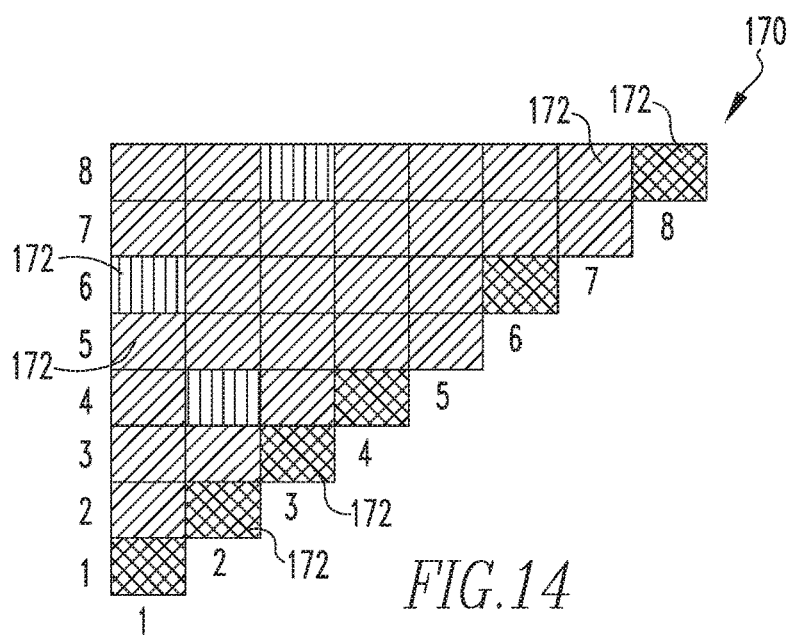
FIG. 14 shows a PMI map according to an exemplary embodiment.

Next, pointwise mutual information (PMI) is used to measure the association between each pair of biomarker patterns in the dictionary, and thus different cell phenotypes, for the subject slide(s). This metric captures general statistical association, both linear and nonlinear, where previous studies have used linear metrics such as Spearman's rho coefficient. Once PMI is computed for each pair of biomarker patterns, a measure of all associations in the data of the subject slide is displayed in a PMI map. An exemplary PMI map 170 is shown in FIG. 14.

PMI map 170 describes relationships between different cell phenotypes within the microenvironment of the subject slide(s). In particular, the entries 172 in PMI map 170 indicate how frequently a particular spatial interaction between two phenotypes (referenced by the row and column number) occurs in the dataset when compared to the interactions predicted by a random (or background) distribution over all phenotypes. Entries in a first color, such as red, denote a strong spatial association between phenotypes, while entries in a second color, such as black, denote a lack of any co-localization (weak spatial association between phenotypes). Other colors may be used to denote other associations. For example, PMI entries 172 colored in a third color, such as green, denote associations that are no better than a random distribution of cell phenotypes over the entire dataset. Additionally, PMI map 170 can portray anti-associations with entries 172 denoted in a fourth color, such as blue (e.g., if phenotype 1 rarely occurs spatially near phenotype 3).

Figure 15:
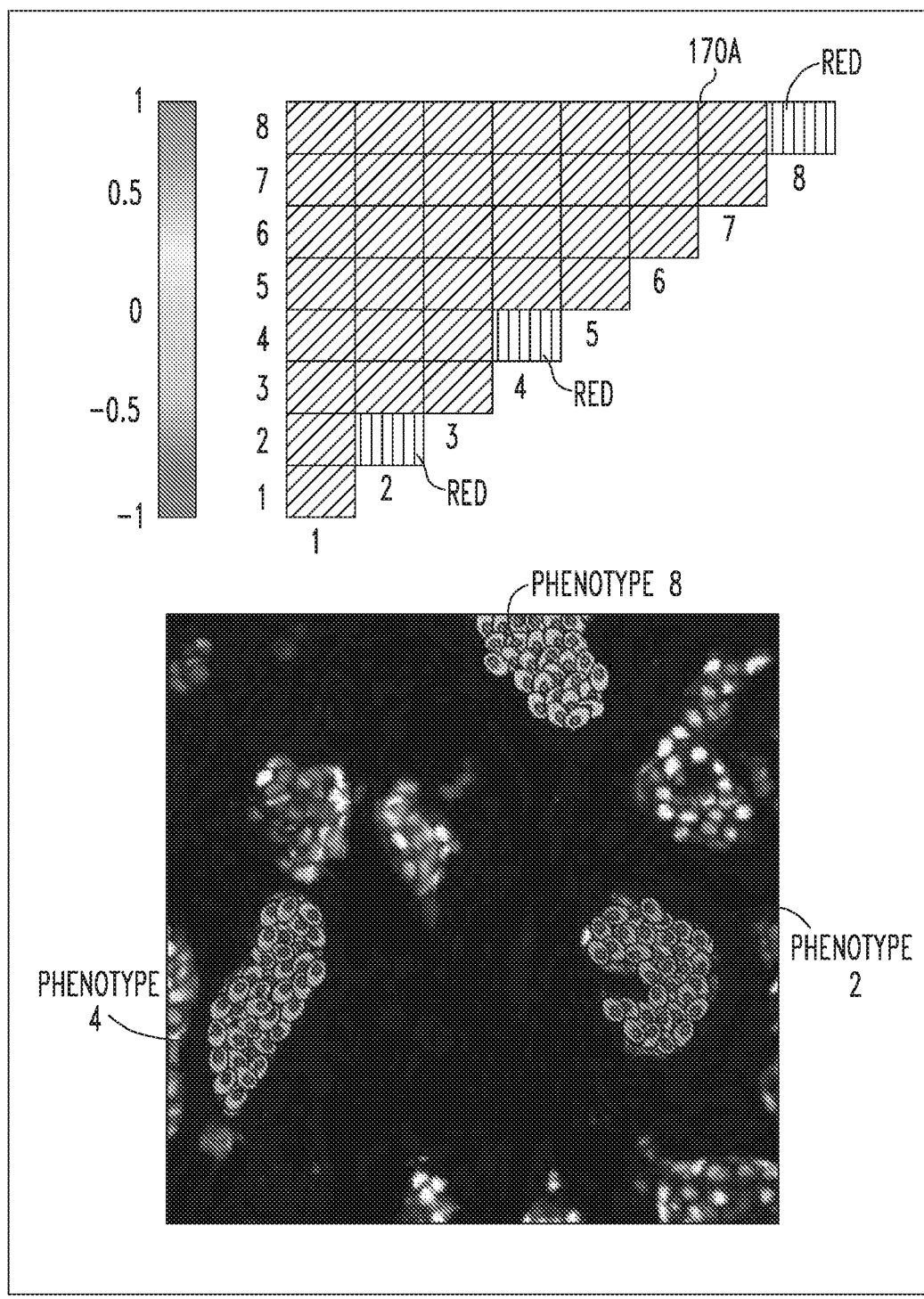
FIGS. 15-17 show exemplary cell spatial dependency images and PMI maps.
Figure 16:
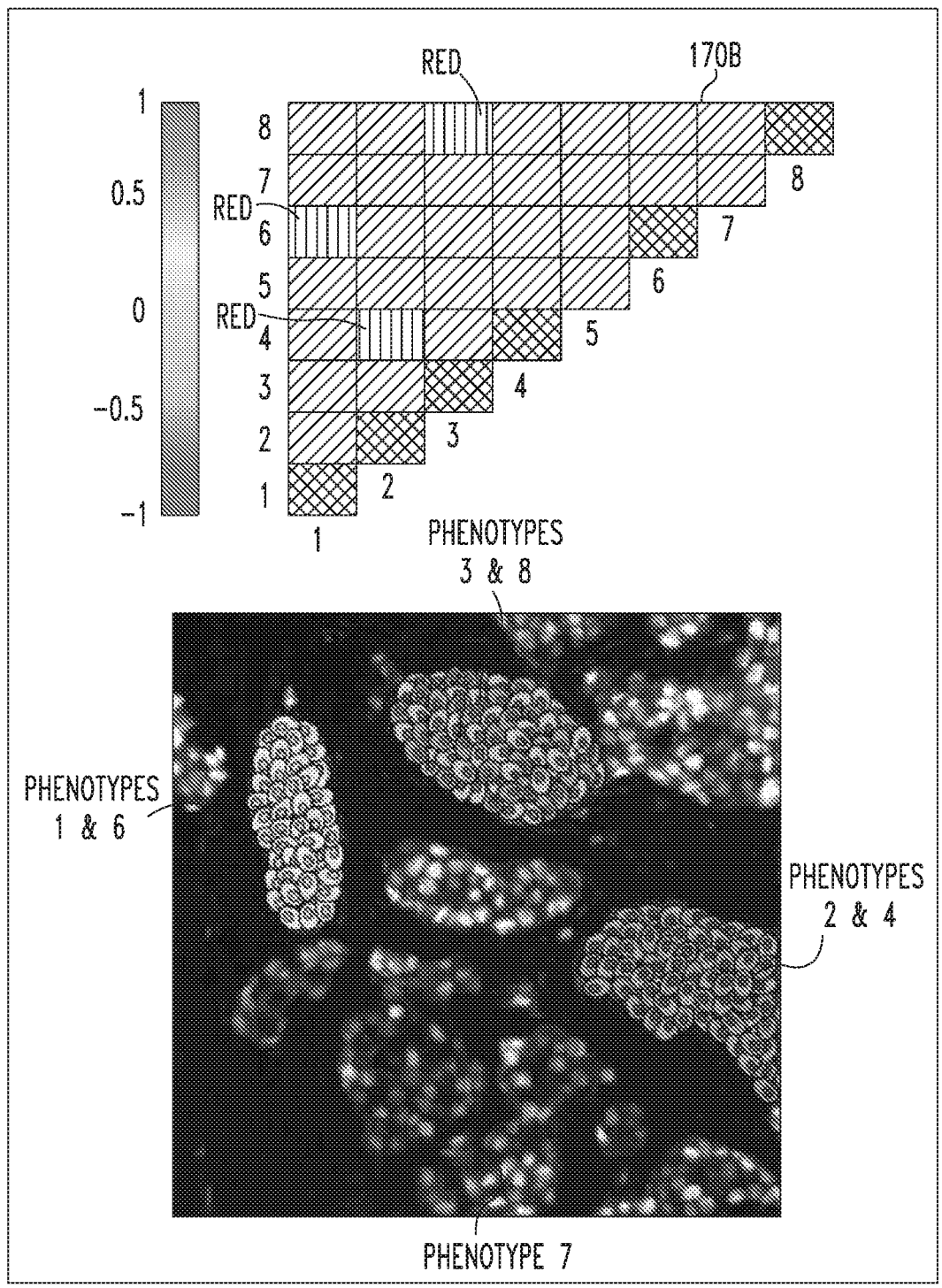
Figure 17:
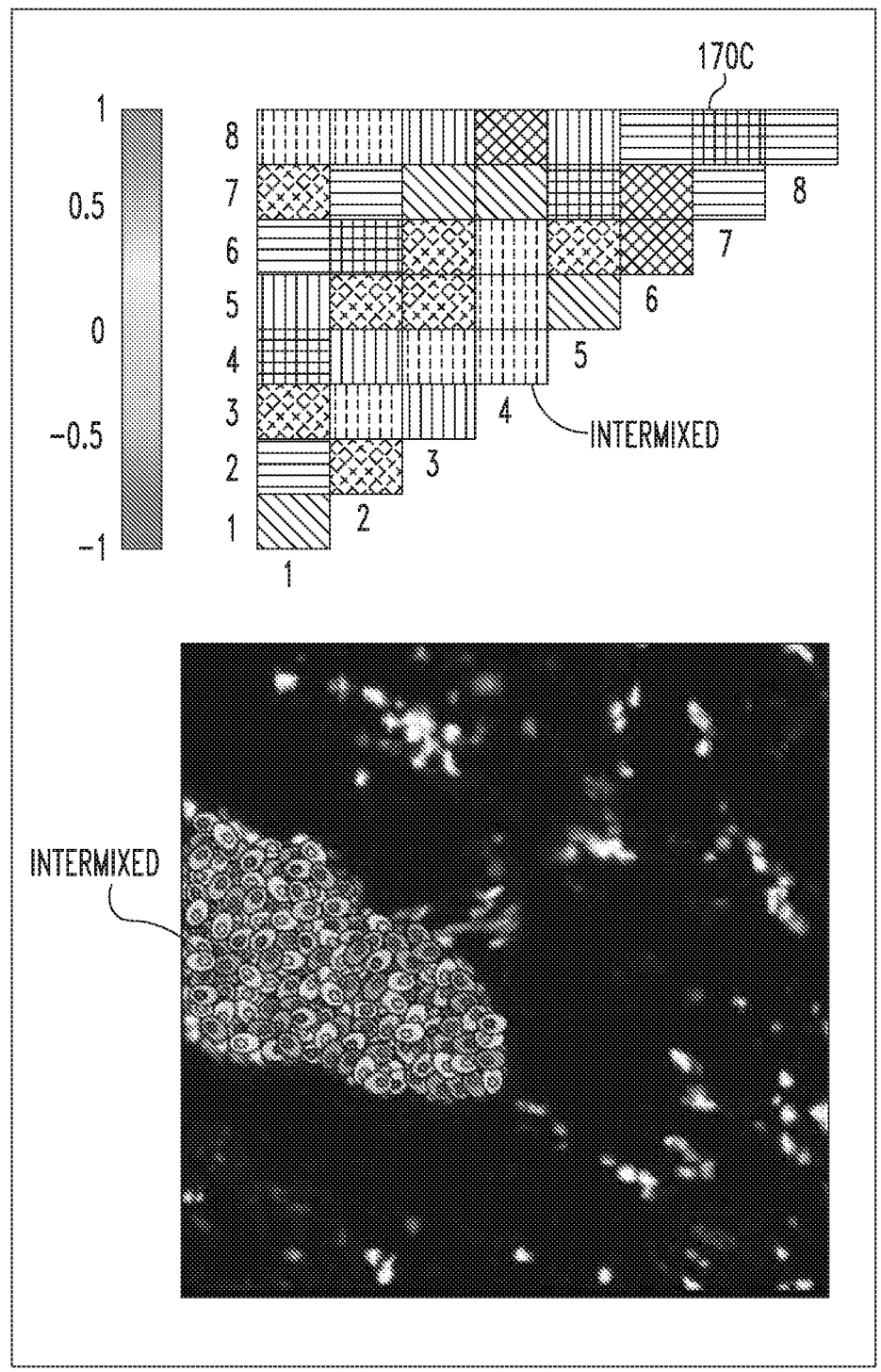

Thus, a PMI map 170 with strong diagonal entries and weak off-diagonal entries describes a globally heterogeneous but locally homogeneous tumor. An example of such a PMI map 170A is shown in FIG. 15. In this example, the associations in the diagonal entries for phenotypes 2, 4 and 8 are strong. This implies that these phenotypes are spatially associated with cells of the same phenotype, as shown by the composition of the individual microdomains in the tumor sample image shown in FIG. 15. On the contrary, a PMI map 170B with strong off-diagonal entries can describe a tumor that is locally heterogeneous. An example of such a PMI map 170B is shown in FIG. 16. In this example, the associations between the cellular phenotypes 1 and 6, the cellular phenotypes 2 and 4, and the cellular phenotypes 3 and 8 are spatially localized. Furthermore, PMI map 170B shows only one association of phenotype 7 cells with itself. Exemplary PMI map 170C shown in FIG. 17 shows associations between all phenotypes in the tumor image and hence PMI map 170C is thoroughly intermixed with colors. The benefit of PMI maps 170 over existing measures is that the maps evoke a spatial relationship between phenotypes. They provide not only a summary of cellular composition, but an approximation of the tumor topology. For the sake of brevity, more complicated PMI map examples have not been included, but it will be understood that all PMI maps 170 are built off of these simple interactions.

In the exemplary embodiment, PMI for the subject slide(s) is calculated as follows. Given a linear deconstruction of an IF dataset X, where each column of X is a cell $x_k$, into an overcomplete dictionary D, where each column of D is a distinct pattern $d_i$, and a sparse coding matrix W which assigns each cell to only a single biomarker intensity pattern, each cell is, as described herein (step 140) assigned to have a phenotype $f_i$ where i is the nonzero index in column $w_k$ of W. A potential pitfall of the algorithm is that high and low signal intensity cells can be assigned to the same cell phenotype. PMI between a pair of biomarker phenotypes ($f_i$, $f_j$) for a given network or network sets is defined as:

$$PMI_s(f_i, f_j) = \log \frac{P(f_{i_s}, f_{j_s})}{P(f_{i_t})P(f_{j_t})},$$

where $P(f_{i_s})$ is the probability of phenotype $f_i$ occurring in network set s, and $P(f_{i_t})$ is the background probability distribution of phenotype $f_i$ derived from the complete ensemble of networks. Note that the background distributions are based on the entire dataset, in order to compare individual networks to the distribution of tissue slide as a whole. This construction is similar to the position-specific scoring matrices (PSSM) for either DNA or protein sequences, where the background distributions denote the probability of finding any particular nucleotide or amino acid over the dataset of sequences, for any given position. A PMI map consists of the PMI score for every possible pair of patterns in the vocabulary for a given network set s. While we advocate the interpretation of the two-dimensional PMI map for a thorough understanding of heterogeneity, we also derive a one-dimensional heterogeneity score value from the PMI map, for convenience of the reader interested in comparing with other one-dimensional scores in the literature. The information-deficient one-dimensional heterogeneity score is defined as:

$$HET_{PMI_s} = \sum_{i,j} \left| \log \frac{P(f_{i_s}, f_{j_s})}{P(f_{i_t})P(f_{j_t})} \right|,$$

where higher scores denote a larger difference from the background distribution. The one-dimensional scores can incorrectly map two spatially different organizations of the TMEs, as seen by their PMI maps, to the same scale.

After computing PMI map 170 for the subject slide(s) and identifying significant interactions or interaction motifs, it is necessary to interrogate the cells which contributed to this significant association. A significant interaction would be considered when the PMI value is close to ±1. PMI values close to 1 signify that this particular spatial interaction of biomarker patterns occurs more frequently than is observed in the background distribution. PMI values close to −1 signifies that when one pattern is observed in the network, that the other pattern is found to be observed less frequently than expected from the background distribution. PMI values close to zero signify interactions that may adequately be described by the background distribution.

C. System Implementations

Figure 18:
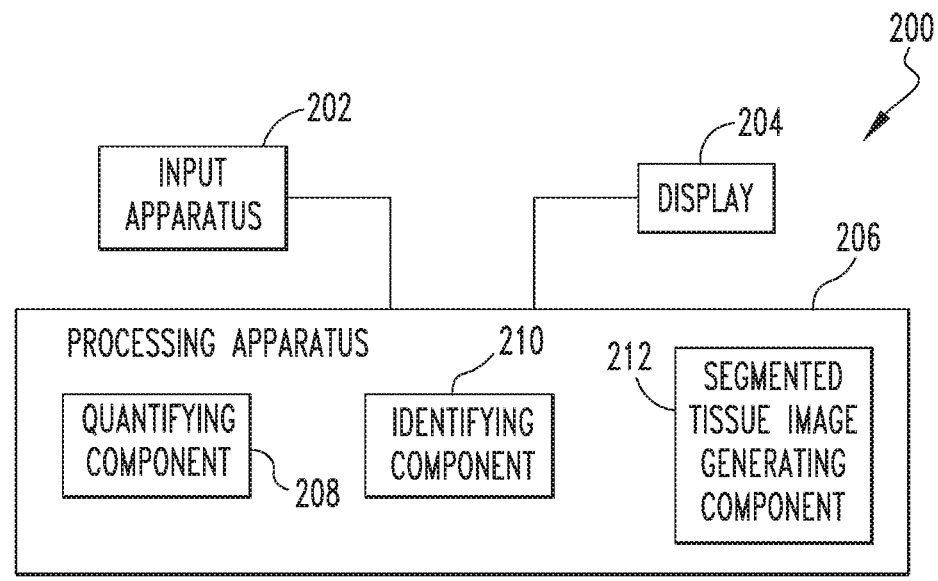
FIG. 18 is a schematic representation of a system for implementing the methodologies for segmenting H&E images described herein.

FIG. 18 is a schematic diagram of an exemplary system digital pathology 200 in which the H&E stained tissue image segmentation methodologies described herein may be implemented. As seen in FIG. 18, system 200 is a computing device structured to receive digital image data representative of H&E stained tissue images and process those images as described herein. System 200 may be, for example and without limitation, a PC, a laptop computer, a tablet computer, a smartphone, or any other suitable device structured to perform the functionality described herein. System 200 includes an input apparatus 202 (such as a keyboard), a display 204 (such as an LCD), and a processing apparatus 206. A user is able to provide input into processing apparatus 206 using input apparatus 202, and processing apparatus 206 provides output signals to display 204 to enable display 204 to display information to the user (such as segmented tissue images) as described in detail herein. Processing apparatus 206 comprises a processor and a memory. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 206 includes a quantifying component 208 configured for quantifying local spatial statistics for H&E stained tissue images as described herein based on received image data representing a H&E stained tissue image, an identifying component 210 configured for identifying histological structures within the H&E stained tissue image based on the local spatial statistics as described herein, and a segmented tissue image generating component 212 configured for generating a segmented H&E stained tissue image using the received image data and the identified histological structures, which image may then be provided to display 204. Quantifying component 208 may include one or more components configured for quantifying local spatial statistics by determining mutual information data indicative of statistical associations between neighboring pixels in the H&E image data, and identifying component 210 may include one or more components configured for identifying histological structures by using the mutual information data and a graph-based spectral segmentation algorithm as described herein. Alternatively, quantifying component 208 may include one or more components for identifying putative nuclei locations from the RGB data in the form of super pixels, building a superpixel graph based on a pointwise distance between each superpixel and a number of its nearest neighbors, and clustering the superpixels into labeled segments, and identifying component 210 may include one or more components configured for identifying by merging the labeled segments into the histological structures as described herein.

Figure 19:
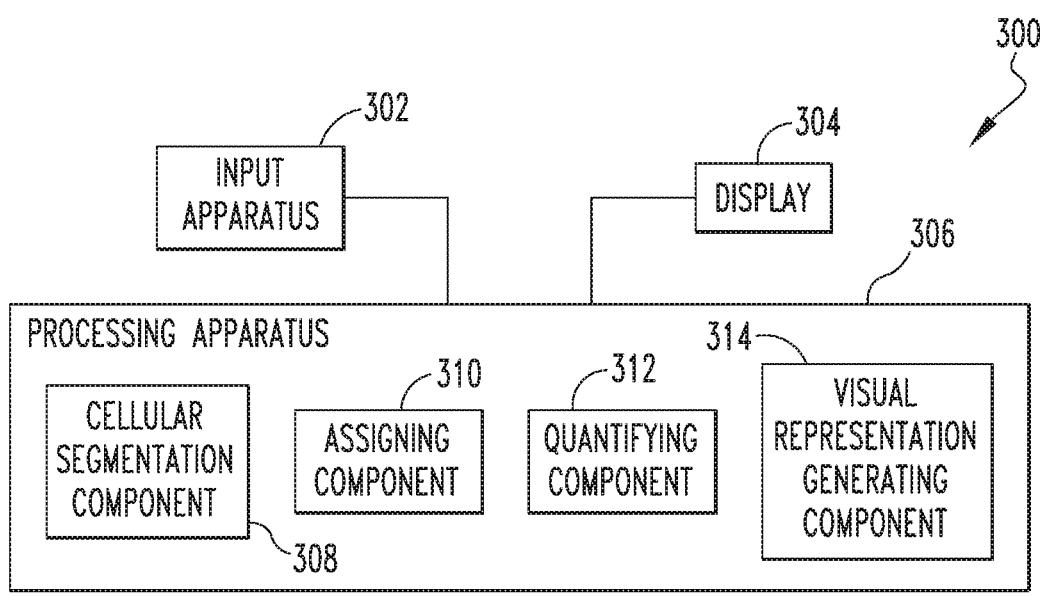
FIG. 19 is a schematic representation of a system for implementing the methodology for quantifying intratumor spatial heterogeneity as described herein.

FIG. 19 is a schematic diagram of an exemplary digital pathology system 300 in which the methodology for quantifying spatial intratumor heterogeneity described herein may be implemented. As seen in FIG. 19, system 300 is a computing device structured to receive digital image data representative of fluorescence tissue images and process those images as described herein. System 300 may be, for example and without limitation, a PC, a laptop computer, a tablet computer, a smartphone, or any other suitable device structured to perform the functionality described herein. System 300 includes an input apparatus 302 (such as a keyboard), a display 304 (such as an LCD), and a processing apparatus 306. A user is able to provide input into processing apparatus 106 using input apparatus 302, and processing apparatus 306 provides output signals to display 304 to enable display 304 to display information to the user (such as spatial dependency images and PMI maps) as described in detail herein. Processing apparatus 306 comprises a processor and a memory. The processor may be, for example and without limitation, a microprocessor (μP), a microcontroller, or some other suitable processing device, that interfaces with the memory. The memory can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. The memory has stored therein a number of routines that are executable by the processor, including routines for implementing the disclosed concept as described herein. In particular, processing apparatus 306 includes a cellular segmentation component 308 configured for performing cellular segmentation on image data representing a number of fluorescence tissue images to identify a plurality of cells of the number of fluorescence tissue images, an assigning component 310 configured for assigning each of the cells to one of a plurality of predetermined biomarker intensity patterns, a quantifying component 312 for quantifying spatial statistics for the number of fluorescence tissue images based on the assigned predetermined biomarker intensity patterns, and a visual representation generating component 314 for generating a visual representation of the quantified spatial statistics, such as a cell spatial dependency image 165 or a PMI map 170. Quantifying component 312 may include one or more components configured for quantifying the spatial statistics by constructing a spatial network to describe an organization of the predetermined biomarker intensity patterns in the number of fluorescence tissue images and quantifying the heterogeneity of the number of fluorescence tissue images by computing pointwise mutual information for each pair of the predetermined biomarker intensity patterns.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of quantifying intratumor cellular spatial heterogeneity in tissue images, comprising:

receiving image data representing a number of tissue images;

performing cellular segmentation on the received image data to identify a plurality of cells of the number of tissue images;

assigning each of the cells to only one of a plurality of predetermined biomarker intensity patterns, wherein the plurality of predetermined biomarker intensity patterns is a set of dominant biomarker intensity patterns learned from control data obtained from a set of cell segmented control images, wherein the control data comprises, for each control image, an intensity level of each of a plurality of predetermined biomarkers for each cell in the control image;

quantifying spatial statistics for the number of tissue images based on the assigned predetermined biomarker intensity patterns including deriving pointwise mutual information as a spatial statistic to quantify spatial intratumor heterogeneity in the number of tissue images; and generating a visual representation of the quantified spatial statistics.

2. The method according to claim 1, wherein the quantifying comprises constructing a spatial network to describe an organization of the predetermined biomarker intensity patterns in the number of tissue images and quantifying the heterogeneity of the number of tissue images by computing pointwise mutual information for each pair of the predetermined biomarker intensity patterns, wherein the visual representation is based on the computed pointwise mutual information for each pair of the predetermined biomarker intensity patterns.

3. The method according to claim 2, wherein the visual representation is a PMI map having a plurality of entries, and wherein the PMI map describes relationships between the predetermined biomarker intensity patterns.

4. The method according to claim 1, further comprising generating a second visual representation that comprises an image showing spatial dependencies among the cells of the number of tissue images using a plurality of schematic representations, each schematic representation corresponding to one of the predetermined biomarker intensity patterns, wherein each of the cells is represented in the second visual representation by only one of the schematic representations.

5. A non-transitory computer readable medium storing one or more programs, including instructions, which when executed by a computer, causes the computer to perform the method of claim 1.

6. The method according to claim 1, wherein the set of dominant biomarker intensity patterns is learned from the data by partitioning the data into a first data partition and a second data partition using biomarker intently level thresholds, learning a first set of dominant biomarker intensity patterns from the first data partition by deriving a first sparse signal representation and data reconstruction for the first data partition, learning a second set of dominant biomarker intensity patterns from the second data partition by deriving a second sparse signal representation and data reconstruction for the second data partition, and determining the set of dominant biomarker intensity patterns from the first set of dominant biomarker intensity patterns and the second set of dominant biomarker intensity patterns using cross validation of the first sparse signal representation and data reconstruction and the second sparse signal representation and data reconstruction.

7. A method of quantifying intratumor cellular spatial heterogeneity in tissue images, comprising:
   receiving image data representing a number of tissue images;
   performing cellular segmentation on the received image data to identify a plurality of cells of the number of tissue images;
   assigning each of the cells to one of a plurality of predetermined biomarker intensity patterns;
   quantifying spatial statistics for the number of tissue images based on the assigned predetermined biomarker intensity patterns; and
   generating a visual representation of the quantified spatial statistics, wherein the quantifying comprises constructing a spatial network to describe an organization of the predetermined biomarker intensity patterns in the number of tissue images and quantifying the heterogeneity of the number of tissue images by computing pointwise mutual information for each pair of the predetermined biomarker intensity patterns, wherein the visual representation is based on the computed point wise mutual information for each pair of the predetermined biomarker intensity patterns, wherein the visual representation is a PMI map having a plurality of entries, and wherein the PMI map describes relationships between the predetermined biomarker intensity patterns, and wherein each of the entries indicates how frequently a particular spatial interaction between two of the predetermined biomarker intensity patterns occurs in the image data when compared to the interactions predicted by a random distribution over all predetermined biomarker intensity patterns.

8. The method according to claim 7, wherein one or more of the entries is depicted in a first color to denote a strong spatial association between predetermined biomarker intensity patterns and one or more of the entries is depicted in a second color to denote a week spatial association between predetermined biomarker intensity patterns.

9. The method according to claim 8, wherein the entries are arranged in a plurality of rows and a plurality of columns.

10. A computerized system for quantifying intratumor cellular spatial heterogeneity in tissue images, comprising:
   a processing apparatus, wherein the processing apparatus includes:
   a cellular segmentation component configured for performing cellular segmentation on image data representing a number of tissue images to identify a plurality of cells of the number of tissue images;
   an assigning component configured for assigning each of the cells to only one of a plurality of predetermined biomarker intensity patterns, wherein the plurality of predetermined biomarker intensity patterns is a set of dominant biomarker intensity patterns learned from control data obtained from a set of cell segmented control images, wherein the control data comprises, for each control image, an intensity level of each of a plurality of predetermined biomarkers for each cell in the control image;
   a quantifying component for quantifying spatial statistics for the number of tissue images based on the assigned predetermined biomarker intensity patterns including deriving pointwise mutual information as a spatial statistic to quantify spatial intratumor heterogeneity in the number of tissue images; and
   a visual representation generating component for generating a visual representation of the quantified spatial statistics.

11. The system according to claim 10, wherein the quantifying component is configured for quantifying the spatial statistics by constructing a spatial network to describe an organization of the predetermined biomarker intensity patterns in the number of tissue images and quantifying the heterogeneity of the number of tissue images by computing pointwise mutual information for each pair of the predetermined biomarker intensity patterns, wherein the visual representation is based on the computed point wise mutual information for each pair of the predetermined biomarker intensity patterns.

12. The system according to claim 11, wherein the visual representation is a PMI map having a plurality of entries, and wherein the PMI map describes relationships between the predetermined biomarker intensity patterns.

13. The method according to claim 10, further comprising generating a second visual representation that comprises an image showing spatial dependencies among the cells of the number of tissue images using a plurality of schematic representations, each schematic representation corresponding to one of the predetermined biomarker intensity patterns, wherein each of the cells is represented in the second visual representation by only one of the schematic representations.

14. The system according to claim 10, wherein the set of dominant biomarker intensity patterns is learned front the data by partitioning the data into a first data partition and a second data partition using biomarker intently level thresholds, learning a first set of dominant biomarker intensity patterns from the first data partition by deriving a first sparse signal representation and data reconstruction for the first data partition, learning a second set of dominant biomarker intensity patterns from the second data partition by deriving a second sparse signal representation and data reconstruction for the second data partition, and determining the set of dominant biomarker intensity patterns from the first set of dominant biomarker intensity patterns and the second set of dominant biomarker intensity patterns using cross validation of the first sparse signal representation and data reconstruction and the second sparse signal representation and data reconstruction.

15. A computerized system for quantifying intratumor cellular spatial heterogeneity in tissue images, comprising:
   a processing apparatus, wherein the processing apparatus includes:
   a cellular segmentation component configured for performing cellular segmentation on image data representing a number of tissue images to identify a plurality of cells of the number of tissue images;
   an assuming component configured for assigning each of the cells to one of a plurality of predetermined biomarker intensity patterns;

a quantifying component for quantifying spatial statistics for the number of tissue images based on the assigned predetermined biomarker intensity patterns; and a visual representation generating component for generating a visual representation of the quantified spatial statistics, wherein the quantifying component is configured for quantifying the spatial statistics by constructing a spatial network to describe an organization of the predetermined biomarker intensity patterns in the number of tissue images and quantifying the heterogeneity of the number of tissue images by computing pointwise mutual information for each pair of the predetermined biomarker intensity patterns, wherein the visual representation is based on the computed point wise mutual information for each pair of the predetermined biomarker intensity patterns, wherein the visual representation is a PMI map having a plurality of entries, and wherein the PMI map describes relationships between the predetermined biomarker intensity patterns, and wherein each of the entries indicates how frequently a particular spatial interaction between two of the predetermined biomarker intensity patterns occurs in the image data when compared to the interactions predicted by a random distribution over all predetermined biomarker intensity patterns.

16. The system according to claim 15, wherein one or more of the entries is depicted in a first color to denote a strong spatial association between predetermined biomarker intensity patterns and one or more of the entries is depicted in a second color to denote a week spatial association between predetermined biomarker intensity patterns.

17. The system according to claim 16, wherein the entries are arranged in a plurality of rows and a plurality of columns.

* * * * *

UNITED STATES PATENT AND TRADEMARK OFFICE
CERTIFICATE OF CORRECTION

PATENT NO. : 10,755,138 B2  
APPLICATION NO. : 15/577838  
DATED : August 25, 2020  
INVENTOR(S) : Chennubhotla et al.

Page 1 of 1

It is certified that error appears in the above-identified patent and that said Letters Patent is hereby corrected as shown below:

In the Claims

Column 21, Line 50, "week" should read --weak--

Column 22, Line 40, "front" should read --from--

Column 22, Line 65, "assuming" should read --assigning--

Column 24, Line 12, "week" should read --weak--

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*